(12) United States Patent
Kou

(10) Patent No.: US 7,375,211 B2
(45) Date of Patent: May 20, 2008

(54) METHOD FOR DETECTION AND QUANTIFICATION OF T-CELL RECEPTOR Vβ REPERTOIRE

(76) Inventor: Zhong C. Kou, 4101 NW. 60th Ave., Gainesville, FL (US) 32653

( * ) Notice: Subject to any disclaimer, the term of this patent is extended or adjusted under 35 U.S.C. 154(b) by 0 days.

(21) Appl. No.: 11/603,435

(22) Filed: Nov. 20, 2006

(65) Prior Publication Data

US 2007/0117134 A1    May 24, 2007

Related U.S. Application Data

(60) Provisional application No. 60/737,968, filed on Nov. 18, 2005.

(51) Int. Cl.
*C07H 21/04*    (2006.01)
*G01N 31/22*    (2006.01)

(52) U.S. Cl. .................... 536/24.33; 422/61

(58) Field of Classification Search .................... None
See application file for complete search history.

(56) References Cited

U.S. PATENT DOCUMENTS

2002/0150891 A1* 10/2002 Hood et al. .................... 435/6

FOREIGN PATENT DOCUMENTS

| WO | WO/9213950 | * | 8/1992 |
| WO | WO/9521623 | * | 8/1995 |
| WO | WO/03/044225 | * | 5/2003 |

OTHER PUBLICATIONS

Goh et al., "Gene Expression profile and identification of differentially expressed transcripts during intrathymic T-cell development by cDNA sequencing analysis," Genomics, 2000, vol. 70, No. 1, pp. 1-18.*

George Jr., James., et al., "Developmental Regulation of Dβ Reading Frame and Junctional Diversity in T Cell Receptor-β Transcripts from Human Thymus", *The Journal of Immunology*, Feb. 15, 1992, vol. 148, No. 4, pp. 1230-1239.

Goodall, J., et al., "Marked Conservation of Complementarity-Determining Region 3 of the β-Chain of TCRs Recognizing a Mycobacterial Heat Shock Protein 60-Derived Peptide with Strong Sequence Similarity to Human Heat Shock Protein 60", *The Journal of Immunology*, 1995, pp. 2329-2338.

Hirokawa, M., et al., "Distinct TCRAV and TCRBV repertoire and CDR3 sequence of T lymphocytes clonally expanded in blood and GVHD lesions after human allogeneic bone marrow transplantation", *Bone Marrow Transplantation*, Dec. 2002, vol. 30, No. 12, pp. 915-923.

Kou, Zhou Chen, et al., "Combination Antiretroviral Therapy Results in a Rapid Increase in T Cell Receptor Variable Region β Repertoire Diversity within CD45RA CD8 T Cells in Human Immunodeficiency Virus-Infected Children", *The Journal of Infectious Diseases*, Feb. 2003, vol. 187, pp. 385-397.

MacCalli, C., et al., "TCR beta-chain variable region-driven selection and massive expansion of HLA-class I-restricted antitumor CTL lines from HLA-A *0201+ melanoma patients", *The Journal of Immunology*, 1997, vol. 158, pp. 5902-5913.

Pannetier, C., et al., "T-cell repertoire diversity and clonal expansions in normal and clinical samples", *Immunology Today*, Apr. 1995, vol. 16, No. 4, pp. 176-181.

Posnett, D., et al., "Clonal Populations of T Cells in Normal Elderly Humans: The T Cell Equivalent to 'Benign Monoclonal Gammapathy'", *Journal of Experimental Medicine*, Feb. 1994, vol. 179, pp. 609-618.

Prochnicka-Chalufour, A., et al., "Biased amino acid distributions in regions of the T cell receptors and MHC molecules potentially involved in their association", *International Immunology*, Sep. 1991, vol. 3, No. 9, pp. 853-864.

* cited by examiner

*Primary Examiner*—Kenneth R. Horlick
*Assistant Examiner*—Molly Baughman
(74) *Attorney, Agent, or Firm*—Saliwanchik, Lloyd & Saliwanchik

(57) ABSTRACT

The invention is a method for detecting and measuring T-cell receptor (TCR) repertoires from mammalian lymphocytes. The method is based on the use of the multiple sets of unique primers to amplify 22 regions of the TCR Vβ region and thereby detect clonal expansions related to antigen stimulation of the immune system. Kits containing sets of primers and specialized analytical statistical software for use in determining clonal expansion in humans and mice are disclosed. The reliability, efficiency and short assay time in using the method is well suited to monitoring immune response to vaccination and therapeutic treatments for immune disorders.

10 Claims, 8 Drawing Sheets

METHOD FOR DETECTION AND QUANTIFICATION OF T-CELL RECEPTOR Vβ REPERTOIRE

This application takes benefit from U.S. provisional application Ser. No. 60/737,968 filed Nov. 18, 2005, the entire contents of which are herein incorporated by reference.

BACKGROUND OF THE INVENTION

1. Field of the Invention

The present invention relates to a method for rapid detection and measurement of clonality of TCR repertoires of mammalian T-cell lymphocytes. The method relies on subsets of unique primers that quantitatively determine the extent of clonal expansions of TCR VβT-cell repertoires.

2. Description of Background Art

T lymphocytes are the primary mediators of cellular immunity in humans and animals. A hallmark of the immune system is its ability to recognize the extensive collection of antigens to which an organism is exposed during its lifetime. T lymphocytes play a central role in graft-versus host disease, where the immune system of a host attacks (reject) implanted tissue from a foreign host, in autoimmune disorders, in hypersensitivity, in degenerative nervous system diseases, and many other conditions occupying an essential role in immune responses to infectious agents (e.g., viruses and bacteria) and in the body's natural defenses against neoplastic diseases.

A T-cell immune response is characterized by one or more particular T-cell(s) recognizing a particular antigen, secreting growth-promoting cytokines, and undergoing a monoclonal (or oligoclonal) expansion to provide additional T-cells to recognize and eliminate the foreign antigen (J Exp. Med 179: 609-618 1991). The T-cell receptors (TCRs) are predictive, in the sense that appropriate receptors exist prior to encountering antigen. TCRs are encoded by multiple gene segments that rearrange during T-cell development and generate most of the antigen receptor diversity. TCRs are composed of α-chain and a β-chain. The human TCR β-chain gene complex includes at least 57 variable (V) gene segments, 2 diversity gene segments, 13 joining gene segments, and 2 consistent gene segments which group into 24 TCR Vβ gene families (Immunology Today 16: 176-181, 1995).

T-cells recognize antigen by major histocompatiblity complex (MHC) molecules through their T-cell receptors (Int Immunol, 3: 853-864). The hypervariable region of TCR Vβ repertoire is encoded by variable (V), diversity (D) and joining (J) genes within the complementary-determining region 3 (CDR) (J Immunol, 49: 149-154, 1999). Therefore, changes in CDR3 size, sequence, and diversity can be used to detect the course of T-cell responses to different antigens. Measurement of the extent of diversity within the TCR repertoire has been applied as a surrogate marker for the integrity of the T-cell immunity (J. Immunol. 148: 1230-1239, 1992).

Molecular analysis of TCR repertoire diversity (clonality) within CDR3 region can serve as a tool to study various diseases related to immune-mediated disorders including tumors, autoimmune diseases, immunization of vaccine and bone marrow, transplantation. Determination of TCR repertoire clonality within CDR3 region has also served as a monitoring tool in tracking curative effects of antiviral or anti-tumor treatments. For example, determination of the change in TCR repertoire clonality has been used to monitor T-cell immune reconstitution in HIV-infected individual following antiviral therapy. HIV infection leads to severe disruption of the TCR repertoire including clonal expansion or clonal exhaustion. It has been demonstrated that the perturbed TCR repertoires can be normalized following a successful therapy (J Infect Dis. Feb. 1:1 87(3):385-97, 2003).

Changes in TCR clonalities following antiviral therapy can be used as an intermediate marker for T-cell immune reconstitution. More importantly, TCR repertoire clonotypes may be used as a diagnostic tool, analogous to serological markers. Following the identification of tumor-specific antigens that are recognized on human tumors by T-cells, small clinical trials of therapeutic vaccination have been carried out using these antigens, mostly in metastatic melanoma patients (J Immunol. June 15; 158(12):5902-13, 1997).

The determination of immunodominant clonotypes represents a novel approach in the study of immune-mediated diseases, such as aplastic anemia (AA), some forms of myelodysplasia (MDS) anti-leukemic immune surveillance, graft-versus-leukemia effects and graft-versus-host disease (GVHD) (Bone Marrow Transplant Dec 30(12) 915-23, 2002). Furthermore, TCR repertoire clonality determination holds promise for applications in vaccine design and detecting T-cell immune responses after immunization and in understanding how clonality repertoires may play protective role in modulating intracellular infections or cancer.

Deficiencies in the Art

Currently, cellular immune responses are determined by measuring cytokine secretion or using assays such as ELISpot. These methods typically lack sensitivity, do not truly and directly monitor changes in TCR clonality, and/or are very complicated and impractical. A sensitive, simple and reliable method to detect and monitor the change of TCR V beta clonality is desirable.

SUMMARY OF THE INVENTION

The present invention addresses one or more of the aforementioned needs by providing a novel method of analyzing the T-cell repertoires. Presently there is no method to quickly detect clonality of TCR repertoire and quantitatively determine the extent of the expanded repertoires (clonotypes). The invention is based on the development of a sensitive and reliable detection method that rapidly determines the changes in clonality of TCR Vβ repertoires and is particularly useful for following vaccinations and therapeutic treatments. It is now possible to monitor the changes in TCR Vβ repertoire clonality so that one can measure the therapeutic effectiveness of any vaccines or therapies for infectious diseases such as HIV/AIDS and hepatitis, cancers, bone marrow transplantations and diabetes, and the like. The method may be practiced alone or combined with well-known techniques; for example, "run-off" reaction techniques, DNA cloning and sequencing procedures.

In particular, the disclosed methods enable quick determination of clonalities in human and mouse expanded T-cell populations (the CDR3 region of the 22 Vβ gene families). Twenty-two (22) non-overlapping, highly-specific forward primers for the variable segment of the "super gene," and thirteen (13) non-overlapping reverse primers for the joining segment have been synthesized. Each PCR reaction is composed of one each of the forward Vβ primers and all 13 of the J primers. The combined primers result in specific amplification of an expanded T-cell clone because a clonal TCR is composed of the identical V-D-J sequence. More significantly, the technology is more sensitive than current methods in determining clonality and does not require special equipment such as DNA analyzers. The method is especially appropriate for clinical monitoring. Most standard methods of assessing and measuring clonality require up to three days to make the measurements and statistical determinations. The TCR method disclosed herein for detection and quantitation of T-cell receptor Vβ repertoires is completed in less than one day.

An additional feature of the invention is the use of analytical quantitation software in combination with the PCR amplification and gel fractionation to provide a significantly statistical determination of the Vβ family clonalities.

The present invention relates to methods for detecting TCR repertoires and includes unique primers that are used in combination with PCR reaction buffers and analytical software for applications to diseases related to antigen-driven clonal expansion in T-lymphocytes. The disclosed methods are powerful tools for monitoring cellular immune responses in mammals following vaccinations, virus infections, and therapeutic treatment for diseases such as infectious diseases, autoimmune diseases, cancer, or bone marrow transplantation. The method has been particularly developed for measurement of human and murine TCR repertoires.

In one aspect, the invention provides a method of rapidly detecting for T-cell clonality in a mammal comprising the steps of obtaining T-cells or their subsets from a subject and generating a clonality assay from each family gene fragment length profile for a T-cell receptor Vβ repertoire in a CDR3 region gene family, The assay profile is compared to a control family gene fragment length profile derived from T-cells of a normal or healthy subject. This determines the presence of clonality in the same variable region gene family as the assay profile and is correlated to a T-cell clonal expansion.

In yet another aspect, the invention provides essential materials for kits useful for performing the method of the invention. The kits are convenient for easily detecting clonality within separated T-cells subsets that may be concealed in unfractionated peripheral blood mononucleotide cell (PBMC) T-cells from individuals. The kits of the invention include specifically designed primers for the CDR3 gene region and reagents for providing optimal amplification conditions for nested PCR amplification. In another aspect, the invention provides a method of quantitative determination using statistical quantitative software to determine the extent of the expanded T-cell clones. Using a method such as GeneScan analysis, data under the curve for each individual Vβ family is obtained, preferably from at least ten or more control subjects, and a standard profile is established. The standard profile typically includes mean, standard deviation and threshold.

The invention provides a method for rapidly detecting for T-cell clonality, and has been particularly designed for determining T-cell repertoires in mammals, including humans and mice. Cells from an individual may be derived in any manner from any source, so long as the cell sample contains T-lymphocytes. Cells may be obtained from a tissue or from any body fluid.

Irrespective of the clonality condition, the PBMC is a preferred source for obtaining T-lymphocyte cells from an individual. One obtains T-cells or their subsets and generates a clonality assay from each TCR Vβ repertoire in the CDR3 region of the gene family. The assay profile is then compared to a control family gene fragment length profile derived from T-cells of a healthy human subject in order to determine presence of the clonality in the same variable region gene family as the assay profile. This is then correlated to a T-cell clonal expansion.

A clonality assay is based on a gene fragment profile from the cells for a TCR Vβ variable region gene family. A "clonality gene fragment profile" for a particular variable region gene family contains three types: polyclonal repertoire, oligoclonal repertoire, and monoclonal repertoire. "Polyclonal repertoire" is a normal repertoire from a human subject without any apparent infectious condition such as a neoplastic condition, autoimmune, or other conditions that would potentiate or suppress a T-cell immune response who has not been treated with an antigen-like material. "Oligoclonal repertoire" is the clonal expanded repertoire from an individual who has an apparent infectious condition; for example a neoplastic condition, autoimmune, or other condition that would potentiate or suppress a T-cell immune response in a subject treated with an antigen-like material. "Monoclonal repertoire" is a highly expanded oligoclonal repertoire.

In a preferred embodiment, a family gene fragment length profile is generated by subjecting cDNA prepared from a tissue sample to a first polymerase chain reaction using a family-specific Vβ primer and a first Jβ primer to amplify DNA encoding T-cell receptor third-complementary-determining-regions of a single Vβ family TCR CDR3. This is followed by a second amplification step using a second polymerase chain reaction employing the family specific Vβ primer and a second Jβ primer and separating DNA fragments from the second polymerase chain reaction by length on a high resolution agarose gel. In both polymerase reactions, a preferred annealing temperature for primer annealing in each PCR cycle is 55° C. and 50° C., for the first and nested PCR amplifications, respectively. $NH_4^+$ in the reaction buffer enhances PCR reaction sensitivity.

At least about 22 distinct beta-chain variable region families have been identified to date in the human genome. These include: Vβ gene family regions Vβ1, Vβ2, Vβ3, Vβ4, Vβ5, Vβ6, Vβ7, Vβ8, Vβ9, Vβ11, Vβ12, Vβ13, Vβ14, Vβ15, Vβ16, Vβ17, Vβ18, V β20, Vβ21, Vβ22, Vβ23, and V-β24.

In similar manner, distinct beta-chain variable region families have been identified in the mouse genome, including Vβ1, Vβ2, Vβ3, Vβ4, Vβ5, Vβ6, Vβ7, Vβ8.1, Vβ8.2, Vβ8.3, Vβ9, Vβ11, Vβ12, Vβ13, Vβ14, Vβ15, Vβ16, Vβ17, Vβ18, and Vβ20.

An important aspect of the invention is the recognition that normal control subjects have a characteristic, polyclonal repertoire profile in all of Vβ gene families. Thus, in practicing the method, it is preferable to conduct DNA cloning and/or sequencing procedures to verify that a clonality condition identified in an individual is a monoclonal or oligoclonal T-cell expansion. Thus it is important to determine whether or not subjects have a normal repertoire for the purposes of serving as a control for comparison against the altered Vβ profiles in diseased or abnormal states. For human subjects at least it is preferable to conduct a routine physical examination and medical history to screen for infections, neoplastic and autoimmune conditions, or other conditions that might potentiate or suppress a T-cell immune response. For murine models, care should be taken that they have not been treated with antigen-like materials. Additionally, there should be a determination of Vβ gene family families to verify that the clonal repertoires are not derived from antigen stimulation.

The method can also be used to monitor changes in clonality profiles, preferably for generating family gene fragment profiles from cells obtained at different times, preferably taken at least at two different times, from the same individual to monitor changes in the profiles. For example, the method can be used to monitor the therapeutic efficacy of antiviral therapeutic treatments. Cells are obtained from a human subject in need of an antiviral therapy for a disorder; a pre-treatment gene fragment profile is determined; a cell sample is obtained after initiating treatment; and pre- and post treatment Vβ repertoire clonality in the same gene family are compared. Successful treatment regimens can be assessed by monitoring change of pre-treatment polyclonal repertoires compared post-treatment oligoclonal and monoclonal repertoires.

There are numerous diseases and other physical conditions involving T-cells where T-cells are implicated in the body's immune response to the disorder; where T-cells and/or T-cell proliferation have a causative role in the disorder; and/or where T-cell antigen or immunodeficiency is associated with the disorder. Such disorders include but are not limited to autoimmune diseases, neoplastic diseases, infectious diseases, hypersensitivity, transplantation and graft-versus-host disease, and cancers such as cancer of the breast, colon, lung, liver, pancreas, skin, etc. Infectious diseases include but are not limited to viral infections caused by viruses such as HIV, HSV, EBV, CMV, influenza, and hepatitis A, B, or C.

Family gene fragment profiles to detect clonality obtained at least at two different times from the same individual are useful for determining T-cell immune responses following vaccine immunizations. To determine effects on clonality after vaccination, one obtains cells from a subject prior to immunization; determines a pre-immunization gene fragment profile; obtains a cell sample from the subject after immunization and compares pre- and post-immunization Vβ repertoire clonality in the same gene family repertoire.

Accordingly, the invention includes a method for detecting T-cell clonality, comprising synthesizing first strand cDNA from a sample containing T-lymphocytes; amplifying the cDNA to produce nested PCR products; further amplifying the nested PCR products with at least 59 primers each specific for one of 22 regions of T-cell Vβ gene CDR3 regions; separating the amplified nested PCR products from among 22 Vβ gene families; and detecting T-cell clonality as at least one of a monoclonal repertoire, an oligoclonal repertoire, or a polyclonal repertoire of Vβ clonal expansion.

The sample is a tissue sample from either a human or a mouse and can be blood or any tissue which contains T-lymphocytes. Depending on the sample, whether human or mouse, selected primers are used to amplify the nested PCR products. While fewer than 59 primers might be used, the results obtained with the at least 59 primers specifically designed for use in detecting mouse or human TCR Vβ repertoires is highly preferred. The primers designed for use with human samples are SEQ ID NOs; 60-118; however, small changes in length or bases of each primer (e.g., lengths from 12-30 nucleotides) are also within the scope of the invention. Primers having sequences identified at SEQ ID NOs: 1-59 have been found to provide outstanding results with mouse samples, although small changes in base composition or length of these primers may also provide equivalent results.

Each primer has been designed to bind to non-overlapping regions of CDR3 T-cell Vβ human or mouse gene.

The invention also incorporates a method for measuring T-cell receptor (TCR) repertoire profiles, comprising the steps of amplifying cDNA encoding TCR third complementarity determining regions of TCR CDR3 of a single Vβ family with a T-cell family-specific Vβ primer and a Jβ primer; further amplifying the nested DNA templates with at least 59 primers comprising Vβ primers and Jβ primers between about 15 and about 28 bases each primer hybridizing with a non-overlapping region of Vβ or Jβ; separating amplified DNA segments; measuring length of separated amplified DNA fragments; spectratyping the DNA; and determining a quantitative TCR Vβ profile by analytical statistical analysis of the data obtained from spectratyping.

The cDNA is from human or mouse T-lymphocytes. The 59 primers for use with the human sample are identified as having the sequence of SEQ ID NOs; 60-118 and the 59 primers for use with the mouse sample as having the sequence of SEQ ID NOs: 1-59.

A practical and convenient use of the invention is a kit for detecting T-cell receptor (TCR) Vβ repertoires. A typical kit will comprise DNA primers having the sequence of SEQ ID NOs: 1-118; PCR amplification buffers; and instructions for use. The primers will be selected for use depending on whether or not the sample is from a human or a mouse.

The kits may also comprise analytical statistical software for quantitation of the detected TCR Vβ repertoires and additional instructions for use of the software.

The new method is useful for monitoring changes in clonality associated with immune system disorders. The procedure includes determining clonality of T-cell Vβ repertoires using the described procedures. One obtains a tissue sample in a subject suspected of having an immune system disorder; measures sequence lengths of amplified DNA products of 22 TCR Vβ repertoires from T-lymphocytes in the sample; spectratypes the DNA products; and statistically analyzes the spectratyped DNA products, thus obtaining a quantitative profile of said products. The clonality and profile determinations are then repeated on a tissue sample from the subject after treatment for the immune system disorder; and clonality changes before and after treatment are compared. Such comparison of clonality allows monitoring of changes associated with treatment of immune system disorders. The method can be used in humans and is useful in mouse models. Typical immune disorders that may be monitored include myelodysplasia, graft versus host disease, aplastic anemia, HIV, diabetes and infectious diseases. Immune changes can also be monitored which arise from parasite, virus or bacterial infections.

DEFINITIONS

T-cell receptor repertoire (TCR): T-lymphocytes respond to peptide fragments of protein antigens that are displayed by antigen presenting cells and MHC molecules. The receptor that recognizes these peptide-MHC complexes is the T-cell receptor (TCR). The TCR β-chain gene complex includes at least 57 variable (V) gene segments, which group into 24 TCR Vβ gene families. These TCR gene families are defined as a TCR repertoire.

Polyclonal repertoires refer to T-cells that express different TCRs, while monoclonal repertoires express the same TCR.

Clonally expanded repertoires: expanded repertoires are those that display clonal changes following antigen stimulation.

AAT is alpha-1-antitrypsin.

DETAILED DESCRIPTION OF THE INVENTION

Figure 1:
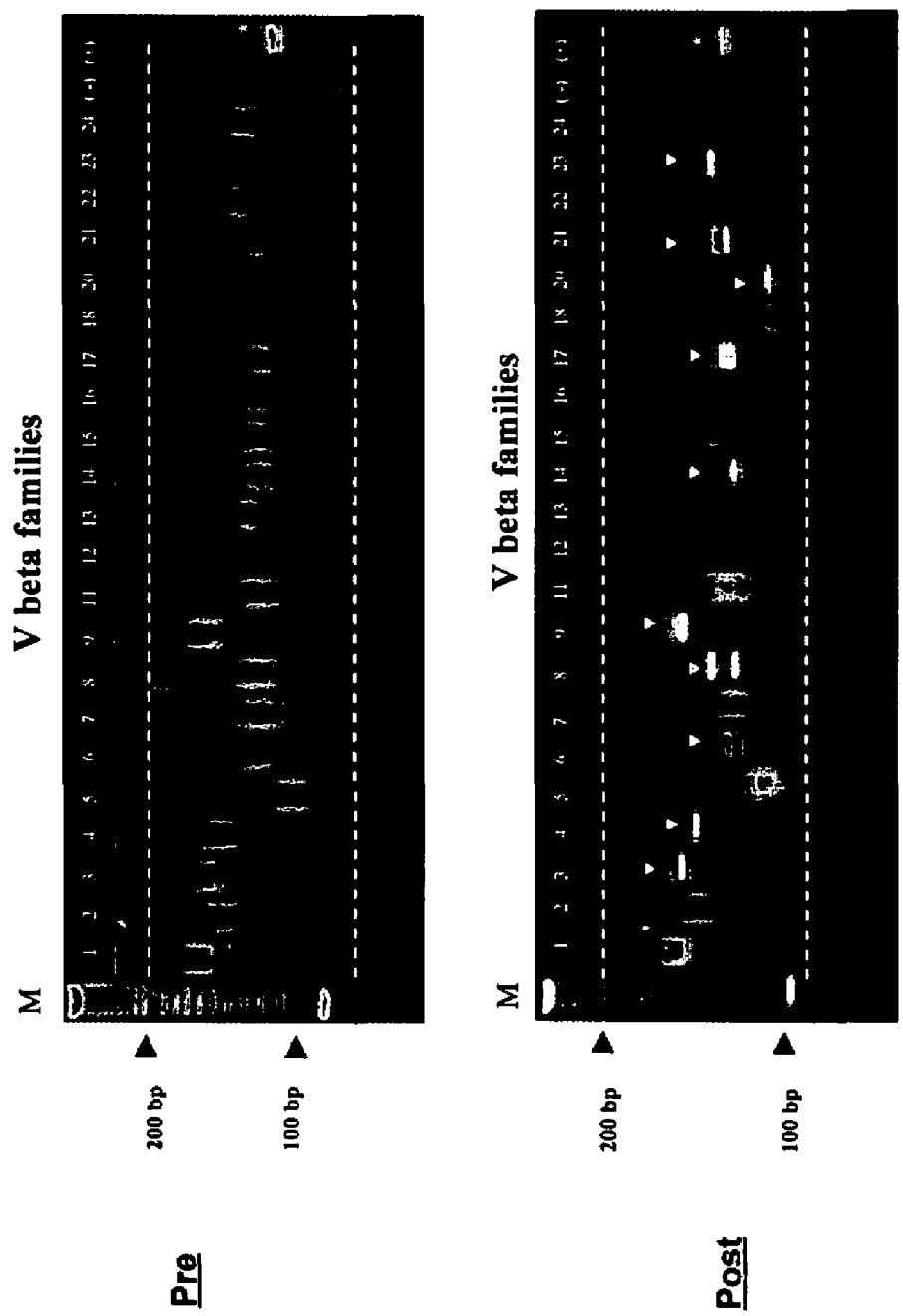
FIG. 1 is a high resolution gel DNA ladder showing clonalities of cDNA for 22 TCR Vβ families in a subject prior to immunization (upper panel) compared with a high resolution gel DNA ladder showing clonalities of cDNA from the same subject post immunization (lower panel).

The present invention describes a procedure for determining clonality of T-cell receptor V beta gene families, and provides the results of the procedure for 22 V beta families in one human subject with vaccination. Clonalities of the TCR Vβ repertoires in CDR3 regions of 22 Vβ families were determine by two step PCR amplifications. cDNA from separated CD4 T-cell subsets of the subject serve as primary PCR templates for the amplifications. Templates of the nested PCR are from the PCR products of the primary amplification.

Clonality of TCR Vβ repertoires was determined by separating the nested PCR products on a high resolution gel. This can be followed in the same subject by determining clonality of 22V beta families with a DNA sequencer and commercially available analytical software. This can be used for detecting T-cell immune response following vaccination in a human subject; e.g., by separating T lymphocytes from blood sample before and after vaccination. Clonalites of 5 TCR Vβ repertoires were analyzed by method described in Example 1. Results showed that polyclonal repertoires in 5 Vβ families (Vβ4, Vβ11, Vβ18, Vβ20, and Vβ23) from the subject before immunization. Clonal expanded repertoires were displayed in the same Vβ families 2 months following vaccination. Results demonstrate vaccination can induce strong cellular immune responses.

The method may be of particular significance in following antiviral therapy in a HIV-infected patient. T lymphocytes were separated from blood from an HIV-infected subject at pre- and post-combination therapy (HEART). 3 TCR clonally expanded repertoires resulting from HIV infection were detected in three families, Vβ7, Vβ9, and Vβ14 using the disclosed method. Ten weeks following anti-viral therapy, the disrupted repertoires were normalized (post 1); the restored repertoires were persistent during the course of anti-viral therapy for 20 weeks (post2). Results support the use of monitoring TCR clonally expanded repertoires as a tracking tool in determining T-cell immune reconstitution following combination therapy in HIV protocols.

The method is useful for detecting T-cell immune response in NOD mouse model following injected AAT. Splenocytes were separated from spleen of NOD mice and clonalites of 5 TCR Vβ repertoires were analyzed in 5 Vβ families (Vβ2, Vβ3, Vβ8.2, Vβ9, Vβ11) from a mouse before injecting peptide. Four weeks after initiation of AAT injections to prevent the development of diabetes, the clonal expanded repertoires displayed in the same Vβ families. These results suggest a potential application of the method described in Example 2 in disease studies in animal models.

T-cell receptors (TCR) are key molecules involving cellular immune responses. TCR repertoires of T lymphocytes of a mammal will change following vaccination or therapeutic treatment. Detection and monitoring changes in TCR repertoires are of prime importance in analyzing cellular immune responses, especially in the context of diseases that have significant effects on the immune system. The disclosed method can rapidly and sensitively detect clonality of the TCR Vβ repertoires in human and mouse T-cells and quantitatively determine the extent of the clonal expansion of the TCR Vβ repertoires.

The disclosed technology is based in part on use of a set of primers that detects not only TCR Vβ clonality but also specifically and rapidly detects and quantitatively determines clonality in the CDR3 region of TCR Vβ families in human and mouse T subsets of CD4 and CD8 T-cell populations. These methods have broad application, including diagnosis, monitoring therapeutic treatment, and drug development. The methods can also be used in preclinical studies with accepted animal models such as mouse diabetic models NOD and EAE mice.

One hundred eighteen (118) uniquely designed primers have been prepared, including 22 Vβ primary primers, nested primers, Cβ primers, and 13Jβ primers for both human and mouse. All primers (SEQ ID NOs: 1-118) are highly specific and do not bind to overlapping regions. The novel primers bind to the antigen specific region, TCRCDR3, so that one obtains specific and sensitive TCR Vβ gene amplification.

The use of PCR with multiple specifically designed primers in the disclosed method is distinguished from standard methods by employing primers in each reaction well. This results in significant increases in specificity and sensitivity of clonality determinations when compared to standard methods.

T-cell clonality is a biological state where T-lymphocytes of an individual expand in response to an antigenic stimulus, or in a neoplastic state where T-cells proliferate autonomously. Thus, clonality conditions may arise in response to a bacterial infection, a viral infection, or parasitic infection. T lymphocytes may expand as an immune response to a vaccination, where an antigen is intentionally introduced. Clonal expansions may also be caused by neoplastic conditions (e.g., cancerous tumors where tumor-infiltrating lymphocytes proliferate), autoimmune disorders and in response to allograft rejection of transplanted cells.

A preferred embodiment includes kits for assaying for T-cell clonality, which can be used to monitor autoimmune, alloimmune, infectious and neoplastic conditions in humans and mice.

Kits designed for detection of human T-cell repertoires include 59 primers, including those having sequences represented by SEQ ID NOs: 60-118, listed in Table 1. The kits may also include standard reagents for performing PCR and, optionally, analytical statistical software, such as software available from BioMed Immunotech, Inc. (Alachua, Fla.), which enables rapid and accurate quantitation of clonal profiles.

Kits for assaying T-cell clonality in murine samples are similar to those for humans, except that the primers included are designed specifically for mice and include primers having sequences represented by SEQ ID NOs: 1-59, listed in Table 1.

TABLE 1

| Sequence ID Number | Sequences |
| --- | --- |
| SEQ ID NO: 1 | CCA GAG CTC ATG TTT CTC TAC AAT C |
| SEQ ID NO: 2 | GTT TTA TAC CTG AAT GCC CAG |
| SEQ ID NO: 3 | CTC TTC CCG GTG CTG ATT ACC TGG C |
| SEQ ID NO: 4 | GCT GCA AGT GGC CAA CAT G |
| SEQ ID NO: 5 | CTT TCA GAA TCA AGA AGT TCT TCA GC |
| SEQ ID NO: 6 | GTG TCC TTC AAA CTC ACC TTG |
| SEQ ID NO: 7 | GTTTCTTCTCAGATCCTCTAAAACC |
| SEQ ID NO: 8 | CAG ATC ACA GCT CTA AAG CC |
| SEQ ID NO: 9 | GGC CTG GTA TCA ACA GAC TCA GGG GC |
| SEQ ID NO: 10 | GTTTCTTCACCGATAGTCGGGTGC |
| SEQ ID NO: 11 | CAG GAT TCA GGG AAA GGA TTG AGA CTG |
| SEQ ID NO: 12 | CGT CTC GAG AGA AGA AGT CAT C |
| SEQ ID NO: 13 | GCT GAT TTA TAT CTC ATA CGA TGT TG |
| SEQ ID NO: 14 | GCA TTT CTC CCT GAT TCT G |
| SEQ ID NO: 15 | GAT GGG TAC AAG GCC TCC AGA C |
| SEQ ID NO: 16 | CTC TCT CAT TCT GGA GTT GGC |
| SEQ ID NO: 17 | GCA CTC AGA AAG CAG ATA TCC CTG |
| SEQ ID NO: 18 | CCA GAC CAA GCC AAG AGA AC |
| SEQ ID NO: 19 | GCA TGG GCT GAG GCT GAT CCA TTA C |
| SEQ ID NO: 20 | GTC CCT GAT GGG TAC AAG GC |
| SEQ ID NO: 21 | GAT TTT GAA CAG GGA AGC TGA CAC |
| SEQ ID NO: 22 | CTG CTC TCT CTA CAT TGG C |
| SEQ ID NO: 23 | GAA GAT TAT GTT TAG CTA CAA TAA TAA G |
| SEQ ID NO: 24 | GCT CAT TTG AAT CTT CGA ATC |
| SEQ ID NO: 25 | TGC AGG GCC TGG AGT TCC TGA CTT AC |
| SEQ ID NO: 26 | CTC AGC TCA GAT GCC GAA TC |
| SEQ ID NO: 27 | CGC AGC AAG TCT CTT ATG GAA GAT GG |
| SEQ ID NO: 28 | TCC ACT CTG AAG ATT CAA CC |
| SEQ ID NO: 29 | TGG ACA TGA TAC CCT TTA CTG GTA TC |
| SEQ ID NO: 30 | TCG ATT TTC TGC TGT GAG GC |

TABLE 1-continued

| Sequence ID Number | Sequences |
| --- | --- |
| SEQ ID NO: 31 | AAA TCA AGC CCT AAC CTC TAC TGG TAC TG |
| SEQ ID NO: 32 | ACG ACC AAT TCA TCC TAA GC |
| SEQ ID NO: 33 | GTTTCTTTCTCAGARCCTCCAGGAC |
| SEQ ID NO: 34 | CCC ATC AGT CAT CCC AAC TTA TC |
| SEQ ID NO: 35 | TCA TGG AGA AGT CTA AAC TGT TTA AG |
| SEQ ID NO: 36 | GTTTCTTCACAGTGAGCCGGGTGCC |
| SEQ ID NO: 37 | CAC ACT GCC TTT TAC TGG TAT CAA CAG AAC |
| SEQ ID NO: 38 | GTTTCTTATTACCAAAAGCCTGGTGC |
| SEQ ID NO: 39 | ATG GCA ACT GCA AAT GAA GGC TCT G |
| SEQ ID NO: 40 | CAT TCT CAA CGT TGA CAG TG 3 |
| SEQ ID NO: 41 | GTTTCTTGAGTCTGGTTCCTTTACC |
| SEQ ID NO: 42 | CCA TAG AGA TCC AGT CCA GC |
| SEQ ID NO: 43 | TGT ATC CCT GAA AAG GGG CAC ACT GC |
| SEQ ID NO: 44 | GCC TGG GAA TCA GAA CGT GC |
| SEQ ID NO: 45 | CAC CCA CCA GCT CAG CTC CAC GTG G |
| SEQ ID NO: 46 | GTT TCT TCT GCT TTT GAT GGC TCA AAC |
| SEQ ID NO: 47 | GTTTCTTCAGCTTTGAGCCTTCACC |
| SEQ ID NO: 48 | GTT CCT CGA ACT CAC AGT GC |
| SEQ ID NO: 49 | GTTTCTTCCTTCTCCAAAATAGAGC |
| SEQ ID NO: 50 | AGC TTG GTA TCG TCA ATC GCC TCA AAA G |
| SEQ ID NO: 51 | GTTTCTTGAGTCGAGTCCCTCTCC |
| SEQ ID NO: 52 | CCA ACC CAC AGC ACT GGA G |
| SEQ ID NO: 53 | GTTTCTTGACGGTGAGTCGTGTCC |
| SEQ ID NO: 54 | CTT TCA GAA TGA AGA CAT CAT CGA C |
| SEQ ID NO: 55 | GTTTCTTCAGTCTGGTTCCTGAGCC |
| SEQ ID NO: 56 | CTC AGT CCA ACA GTT TGA TGA C |
| SEQ ID NO: 57 | GTTTCTTGGAGCCGAGTGCCTGGCC |
| SEQ ID NO: 58 | CCT CAA GTC GCT TCC AAC C |
| SEQ ID NO: 59 | GTTTCTTAACCGTGAGCCTGGTGGC |
| SEQ ID NO: 60 | GTGTACTGGTACCAACAGAGC |
| SEQ ID NO: 61 | GAACCTCTGTGAAGATCGAGTG |
| SEQ ID NO: 62 | GTGTCCAGGATATGGACCATG |
| SEQ ID NO: 63 | GCCAAGTCACCATGATGTTCTG |
| SEQ ID NO: 64 | CAGTATTATGAGAAAGAAGAG |
| SEQ ID NO: 65 | CTGAACACAACCGCCTTTATTGG |
| SEQ ID NO: 66 | CAAGACACCTGGTCATGGGAATG |
| SEQ ID NO: 67 | CTGGTACAGACAGACCATGATGC |

TABLE 1-continued

| Sequence ID Number | Sequences |
|---|---|
| SEQ ID NO: 68 | GGTCACACAGATGGGAAACGAC |
| SEQ ID NO: 69 | GGAATGTTCTCAAACCATGGGCC |
| SEQ ID NO: 70 | CATGGGCTGAGGCTAATCCATTAC |
| SEQ ID NO: 71 | GCCCAGGATATGAACCATAACTAC |
| SEQ ID NO: 72 | GTCCTGGTATCGACAAGACCCAG |
| SEQ ID NO: 73 | GGAGAGATCTCTGATGGATACAG |
| SEQ ID NO: 74 | CAGGATGAGTCCGGTATGCCCAAC |
| SEQ ID NO: 75 | CAGGGCAAGGGCTGAGATTGATC |
| SEQ ID NO: 76 | GTTTACTGGTATCGGCAGCTCCCAG |
| SEQ ID NO: 77 | GGTATTGGCCAGATCAGCTCTG |
| SEQ ID NO: 78 | GGTGCAATCCTATTTCTGGCCAC |
| SEQ ID NO: 79 | GACAGGAAGTGATCTTGCGCTGTG |
| SEQ ID NO: 80 | CATCCCTGATCGATTCTCAGCTC |
| SEQ ID NO: 81 | GTTTCTTTGAGCCGTGTCCCTGGCC |
| SEQ ID NO: 82 | CTCCGAGAGCCCGTAGAACTGGACTTG |
| SEQ ID NO: 83 | TTCCCTGACTGCACTCTG |
| SEQ ID NO: 84 | GTTTCTTCACTGAGAGCCGGGTCCC |
| SEQ ID NO: 85 | CCCTGATTCTGGAGTCCGCC |
| SEQ ID NO: 86 | GCCCAAACCTAACATTCTC |
| SEQ ID NO: 87 | GTTTCTTCACCAGGAGCCGCGTGCC |
| SEQ ID NO: 88 | GGATCTTTCTCCACCTTG |
| SEQ ID NO: 89 | CTCACTTATGCCTTCACC |
| SEQ ID NO: 90 | GCATCATTCTCCACTCTG |
| SEQ ID NO: 91 | GTTTCTTGAGCTGGGTTCCACTGCC |
| SEQ ID NO: 92 | GACGGAGCATTTTCCCCTG |
| SEQ ID NO: 93 | GTTTCTTGAGCCAACTTCCCTCTCC |
| SEQ ID NO: 94 | CCAGATCAACCACAGAGG |
| SEQ ID NO: 95 | CAACCAGACCTCTCTGTAC |
| SEQ ID NO: 96 | GTTTCTTGAGTCGAGTCCCAT |
| SEQ ID NO: 97 | GAGGGACGTATTCTACTC |
| SEQ ID NO: 98 | GTTTCTTAACCTGGTCCCCGAACC |
| SEQ ID NO: 99 | GTTTCTTGAGCCTGGTGCCCGGCC |
| SEQ ID NO: 100 | GCTCCTTCTCAGTGACTC |
| SEQ ID NO: 101 | GTTTCTTGAGTCTGGTGCCTTGTCC |
| SEQ ID NO: 102 | CAGTTGAAAGGCCTGATGG |
| SEQ ID NO: 103 | CAGTGACTATCATTCTGAAC |
| SEQ ID NO: 104 | GCCGAACACTTCTTTCTGC |
| SEQ ID NO: 105 | GTTTCTTAAACACAGCGACCTCGGGTG |
| SEQ ID NO: 106 | GAAAGGAGTAGACTCCACTC |
| SEQ ID NO: 107 | GGAATCCTTTCCTCTCACTG |
| SEQ ID NO: 108 | GGAGTCGCTACCAGCTCCC |
| SEQ ID NO: 109 | CAGTTCCAAATCGCTTCTC |
| SEQ ID NO: 110 | CAGGCTAAATTCTCCCTG |
| SEQ ID NO: 111 | GTTTCTTGAGCCTGGTCCCGTTCCC |
| SEQ ID NO: 112 | GAAAGCCAGTGACCCTGAGTTG |
| SEQ ID NO: 113 | AGTGCCCATCCTGAAGAC |
| SEQ ID NO: 114 | GTTTCTTCAGCCTAGAGCCTTCTCC |
| SEQ ID NO: 115 | GTTTCTTACTGTCAGCCGGGTTGCC |
| SEQ ID NO: 116 | GTGAACGCCTTGTTGCTGG |
| SEQ ID NO: 117 | GTGCGAGGAGATTCGGCAG |
| SEQ ID NO: 118 | GTTTCTTCACGGTCAGCCTGCTGCC |

EXAMPLES

The following examples are provided as illustrations of the invention and are in no way to be considered limiting.

Materials and Methods

H Plate I precoated with primers having sequences SEQ ID NOs: 60,61,62,63,64,65,66,67,68,69,70,71,72,73,74,75, 76,77,78,79,80,82, and 83-118 (available from BioMed Immunotech, Inc., Alachua, Fla.)

HC Plate II precoated with SEQ ID NOs 81,84,85,86, 87,88,89,90,91,92,93,94,95,96,97,98,99,100,101,102,103, 104,105,106,107,108,109,110,111,112,113,114,115,116,117, and 118 (available from BioMed Immunotech, Inc., Alachua, Fla.)

HQ Plate II precoated with SEQ ID NOs 81,84,85,86, 87,88,89,90,91,92,93,94,95,96,97,98,99,100,101,102,103, 104,105,106,107,108,109,110,111,112,113,114,115,116,117, and 118 and 6 FAM (available from BioMed ImmunoTech, Alachua, Fla.)

M Plate I precoated with primers having SEQ ID NOs: 1,2,3,4,5,6,7,8,9,10,11,12,13,14,15,16,17,18,19,20,21,22, and 23 primers having sequences SEQ ID NOs. 1-59 (available from BioMed Immunotech, Inc., Alachua, Fla.)

MQ Plate II precoated with primers having SEQ ID Nos: 24,25,26,27,28,29,30,31,32,33,34,35,36,37,38,39,40, 41,42,43,44,45,46,47,48,49,50,51,52,53,54,55,56,57,58, and 59 (available from BioMed Immunotech, Inc., Alachua, Fla.)

MQ Plate II precoated with primers having SEQ ID Nos. 24,25,26,27,28,29,30,31,32,33,34,35,36,37,38,39,40,41,42, 43,44,45,46,47,48,49,50,51,52,53,54,55,56,57,58, and 59 and 6 FAM (available from BioMed ImmunoTech, Alachua, Fla.)

Example 1

TCR Vβ gene Clonality Determination in Vaccinated Subjects

This example illustrates a new clonality determination procedure for 22 Vβ families in a vaccinated human subject.

Clonalities of the TCR V β repertoires in CDR3 regions of 22 Vβ families were determined by two step PCR amplifications. cDNA from separated CD4 T-cell subsets served as primary PCR templates for the amplifications. The PCR products of the primary amplification served as templates for the nested PCR. Clonality of the TCR Vβ repertoires was determined by separating the nested PCR products on high resolution gel. This example illustrates detection of clonalites of 22 TCR Vβ families in purified CD4 T-cells from a human subject prior to and following vaccination with HAV vaccine.

Separated cDNA from a pre-immunized human was amplified in 22 Vβ families and PCR products (98-196 bp) were separated using a high resolution agarose gel (FIG. 1). A DNA ladder (M) is shown in the first lane of FIG. 1. 22 Vβ families showed a polyclonal smear bands (upper panel), while a monoclonal repertoire a from JurkaT-cell line used as a positive control displayed a clonally expressed single clear band from the Vβ8 gene family, indicated with a star *.

Post immunization, the cDNA was amplified in 22 Vβ families using the multiprimer method of amplification for clonality detection in the same subject. A 10 bp DNA ladder (M) is shown in the first lane of FIG. 1. Arrows (lower panel) indicate that the vaccination resulted in a selected T-cell immune response in 22 Vβ families. Vβ3, 4, 14, 20, and 23 displayed monoclonal expansion and Vβ36, 8, 9, 17, and 21 demonstrated oligoclonal expansion.

Example 2

Clonality of Vβ gene families in Treated and Untreated Mice

Figure 2:
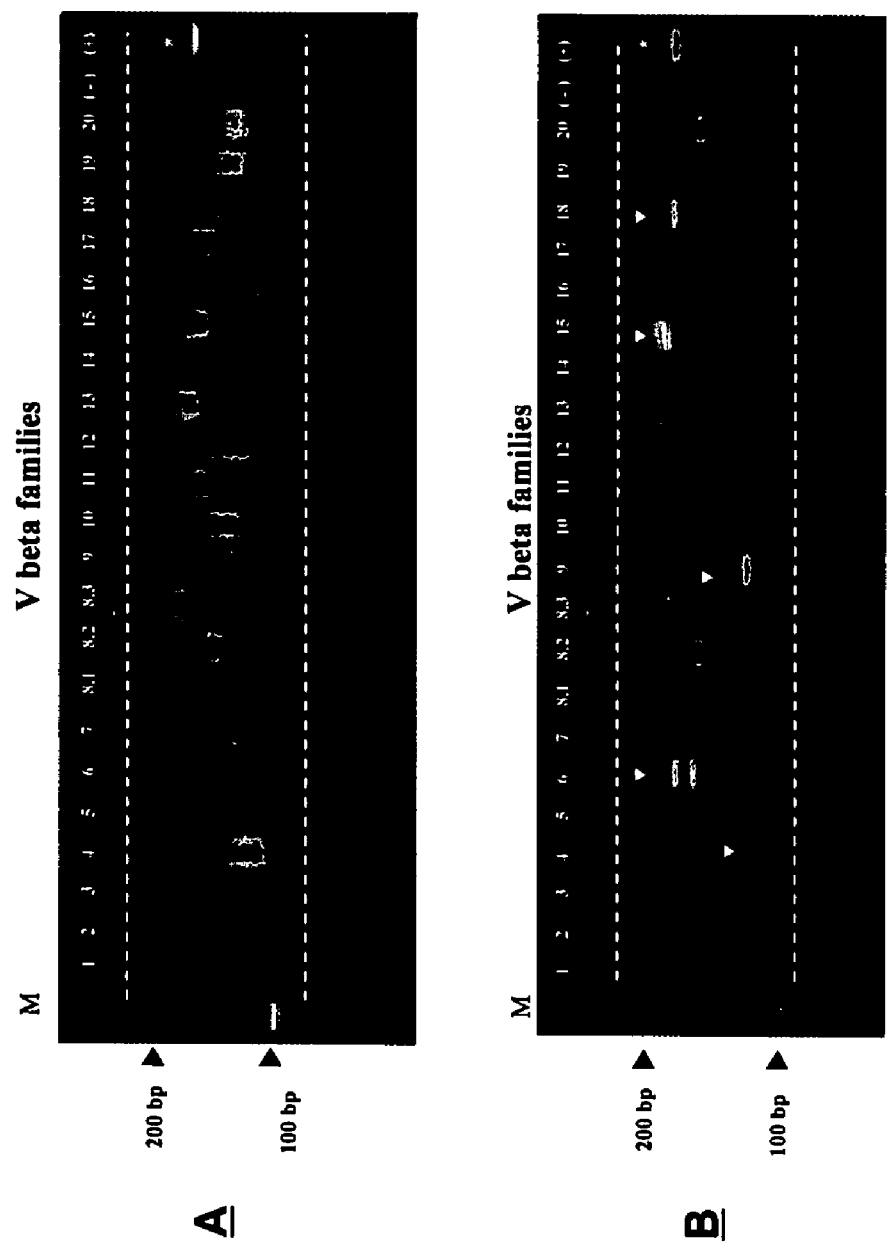
FIG. 2 shows clonalities of 22 TCR Vβ families in splenocytes from untreated NOD mice (upper panel) compared with untreated with the 22 TCR Vβ families in splenocytes from NOD mice after treatment with AAT (lower panel).

T-cell clonality detection in splenocytes from NOD mice was determined as in Example 1. In the untreated mouse, cDNA was amplified in 22 Vβ families and PCR products (105-189 bp) were separated using a high resolution agarose gel (FIG. 2, upper panel). A DNA ladder (M) is shown in the first lane. 22 Vβ families showed polyclonal smear bands, while a monoclonal repertoire from a mouse T-cell line used as a positive control clonally expressed Vβ1 gene family displayed a single clear band, as indicated with a star *. In a mouse treated with AAT, cDNA was amplified in 22 Vβ families and PCR products (105-189 bp) were separated using high resolution agarose gel (FIG. 2, lower panel). A DNA ladder (M) is shown in the first lane. Arrows indicate that the AAT treatment results in a selected T-cell immune response in the 22 Vβ families. Vβ4, 9 and 18 show a monoclonal repertoire and Vβ6 and 15 indicate an oligoclonal repertoire.

Example 3

Comparison of Gene Sequencing and Gel-Based Detection

Figure 3:
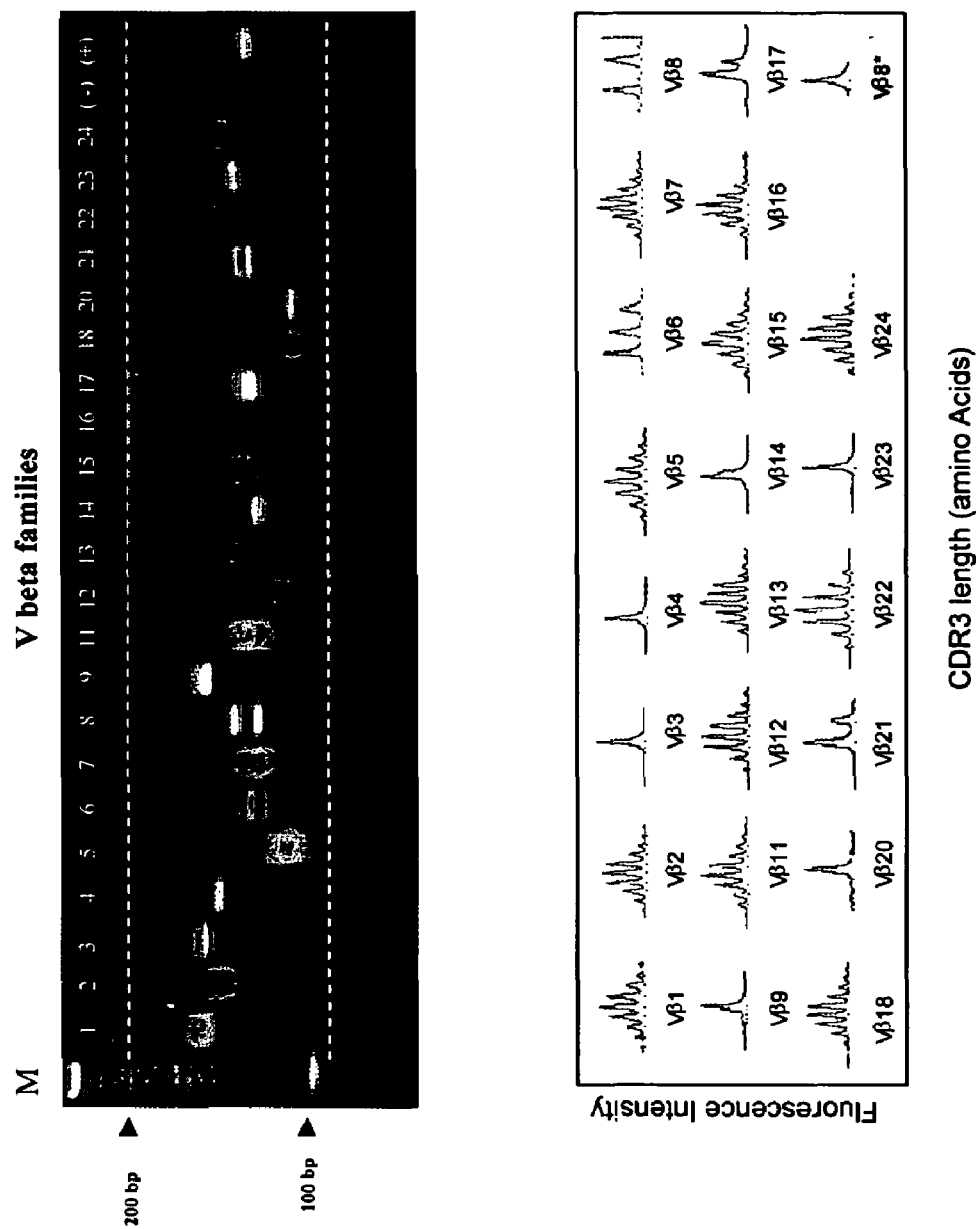
FIG. 3 compares gel based detection sequencing of DNA (lower panel) with conality determination using multiprimer method described herein (upper panel).

A GeneScan assay with an ABI 377 DNA sequencer was compared in the same samples with gel-based detection on the same samples. The results were virtually identical between the gel-based method (FIG. 3, upper panel) and the DNA sequencer-based assay (FIG. 3, lower panel). A single band TCR V β repertoire (upper panel) corresponded to a single peak in the lower panel (see Vβ3, 4, 14, 20, 23, and positive control). The simple DNA fragment set corresponded to the detected peak profile (see Vβ6, 8, 9, 17, 21). The multiple peaks (Gaussian distributions) corresponded to the smear DNA fragments (see Vβ2, 5, 7, 11, 12, 13, 15, 16, 18, 22, and 24).

Example 4

Clonality after HAV Vaccination

Figure 4:
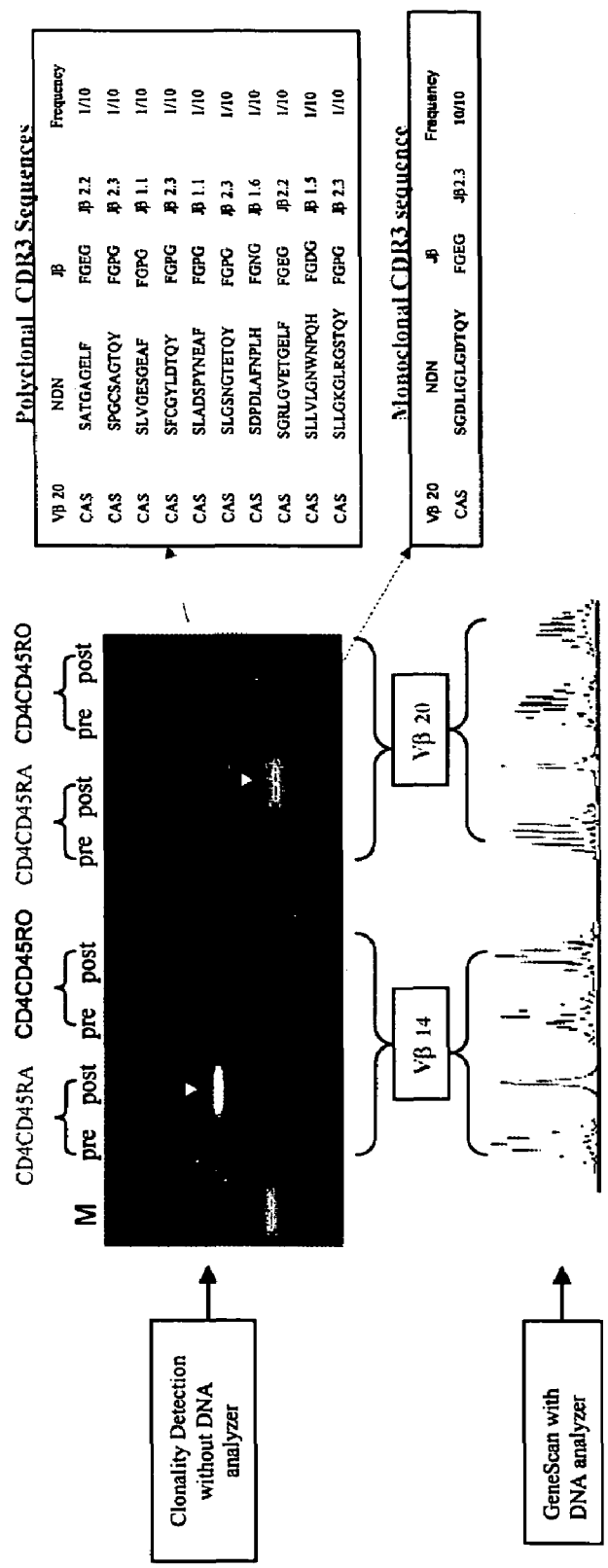
FIG. 4 shows T-cell immune responses in a subset of T-cells following vaccination with HAV vaccine Two representative Vβ families, Vβ14 and Vβ20, show the clonal dominants in the CD4CD45RA T-cell subset (indicated by arrows in the gel image panel) but not in the CD45RO T-cells.

A T-cell immune response in a subset of T-cells following vaccination with HAV vaccine (a neo-antigen) in a human subject was determined. Two representative Vβ families, Vβ14 and Vβ20, show clonal dominants in the CD4CD45RA T-cell subset (FIG. 4, indicated by arrows in the gel image panel) but not in the CD45RO T-cells following vaccination. The polyclonal CDR3 sequences form a smear in agarose gel, but the monoclonal sequence presents as a single clear band (see Vβ20) in the gel image.

Example 5

Quantitative Analysis of Clonal Expansion Products

Figure 5:
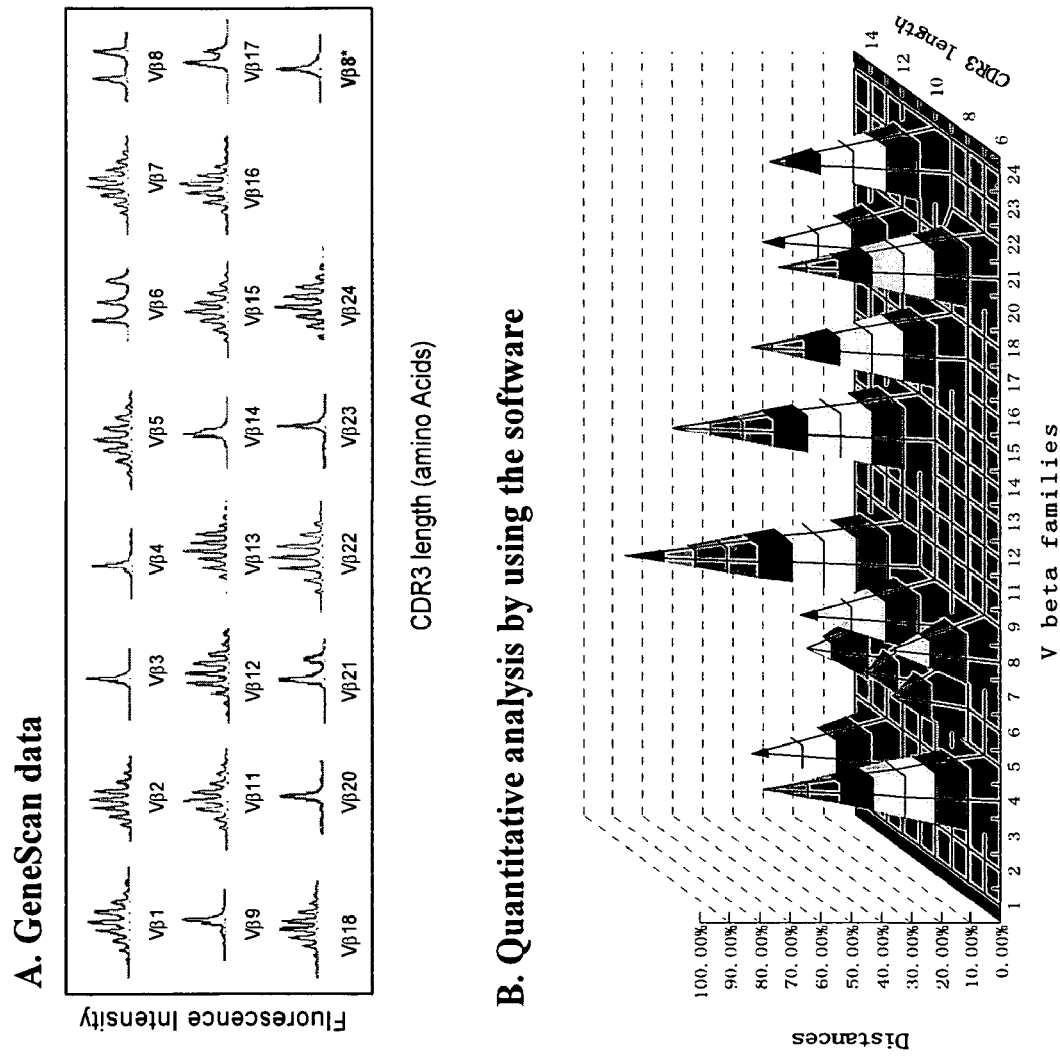
FIG. 5 shows fluorescent labeled PCR products scanned using a DNA sequencer (upper panel). The lower panel shows a three-dimensional landscape obtained from scanned data analyzed by an analytical statistics software.

Fluorescently labeled PCR products were scanned using a DNA sequencer. Results are shown in FIG. 5 (upper panel). The scanned data were then collected and analyzed using quantitative analytical statistics software (available from BioMed Immunotech, Inc., Alachua, Fla.), providing a three-dimensional landscape (FIG. 5, lower panel). The extent of the expanded clonotypes and CDR3 size in TCR Vβ repertoires is seen in FIG. 5, (upper panel). The x-axis displays the 22 Vβ families while the Y-axis corresponds to CDR3 lengths from 6 to 15 amino acids. The Z-axis is the distance (D %) value measuring the extent of clonal expansion.

Example 6

Comparison of Pre and Post vaccination Clonalities

Figure 6:
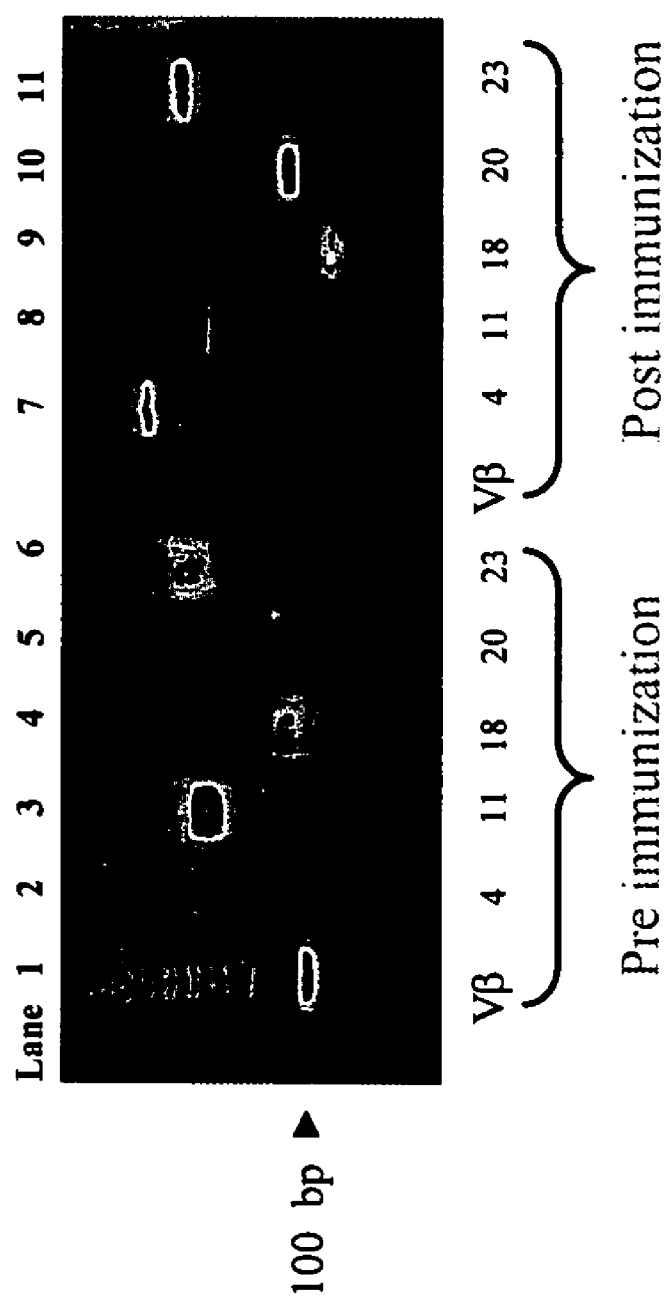
FIG. 6 is a comparison of clonalities from TCR Vβ repertoires in a human subject pre-and post-vaccination.

This example compares clonalities in TCR Vβ repertoires between pre- and post-vaccination from a human subject. T-lymphocytes were separated from blood of a male subject before and after vaccination. Clonalities of 5 TCR Vβ repertoires were analyzed by the method described in previous examples. Results showed polyclonal repertoires in 5 Vβ families (Vβ4, Vβ11, Vβ18, Vβ20, and Vβ23) from the subject before immunization (FIG. 6). A strong cellular immune response 2 months after vaccination was indicated in the clonal expanded repertoires displayed in the same Vβ families (FIG. 6).

Example 7

TCR Vβ repertoire Changes During HAART Treatment

Figure 7:
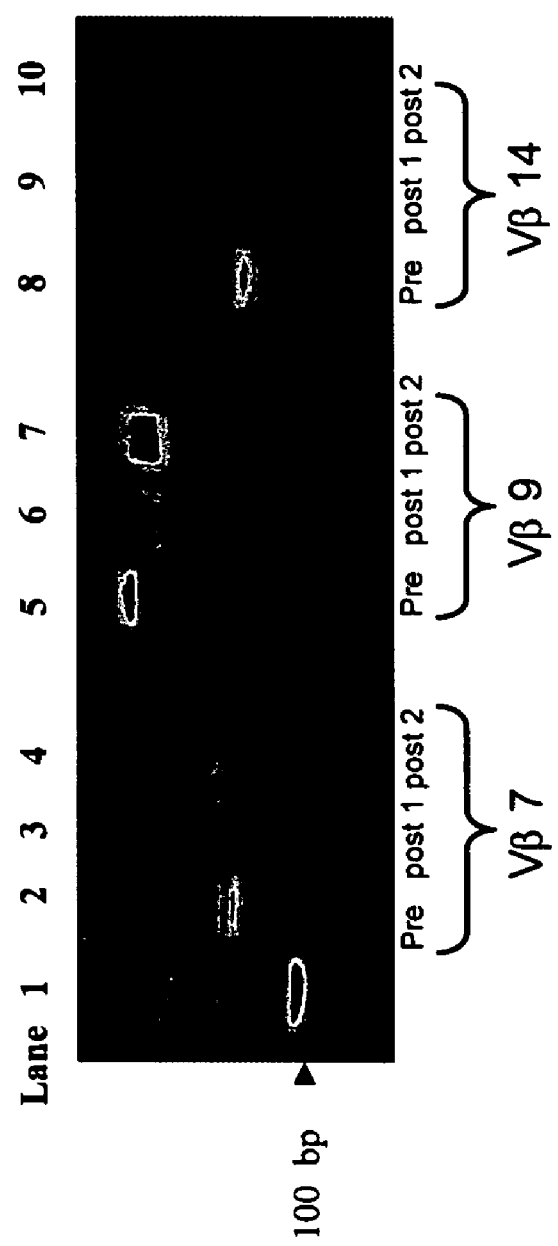
FIG. 7 shows a single DNA band prior to HEART therapy therapy (lanes 2, 5, and 8) in an HIV-infected patient while the restored repertoire displayed smear DNA fragments following HEART (lanes 3,4,6,7,9, and 10).

A longitudinal evaluation of clonality was performed in an HIV-infected patient receiving HEART. Successful therapy in the subject population resulted in a decline in virus load to undetectable levels (<50 copies/ml.) and importantly, the polyclonal repertoire in CD4 T-cells was reestablished within 8 weeks of the initial treatment. Clonal repertoires of Vβ7, 9 and 14 (FIG. 7) showed single DNA band in the patient before HEART therapy (FIG. 7, lanes 2, 5, and 8) while the restored repertoire displayed smear DNA fragments following HEART (lanes 3,4,6,7,9, and 10).

Example 8

TCR Vβ repertoires in Mice Before and After Injection of AAT

Figure 8:
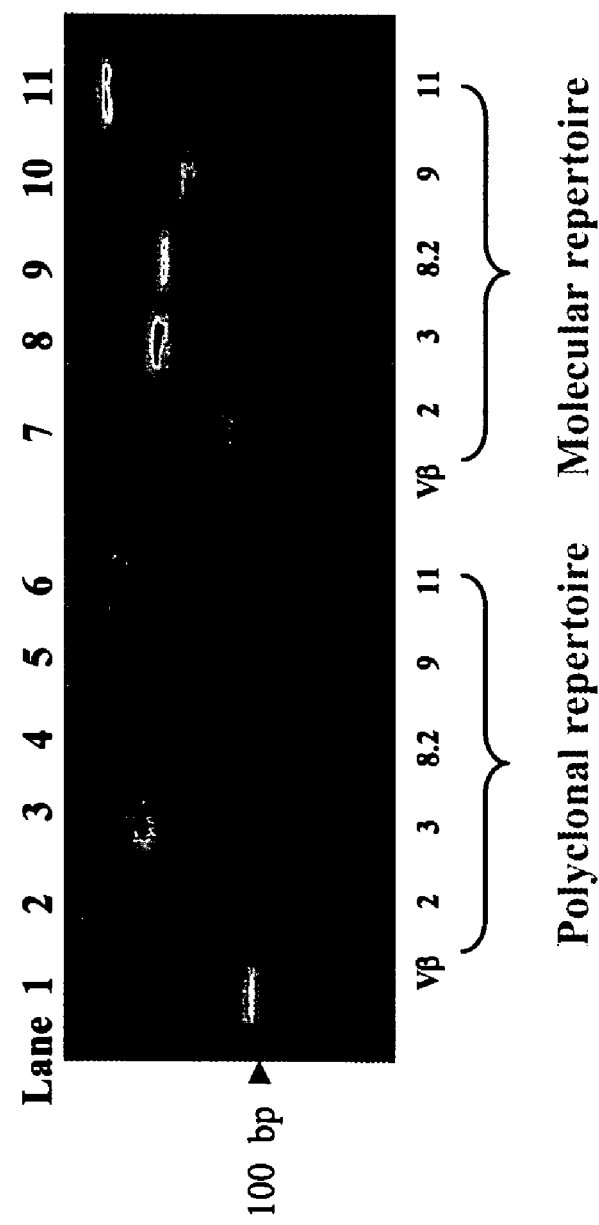
FIG. 8 is a comparison of clonalities of TCR Vβ repertoire in mouse splenocytes pre- and post-injection of AAT.

Comparison of clonalities of TCR Vβ repertoire in mouse splenocytes between pre- and post-injecting AAT. Splenocytes were separated from the spleen of NOD mice. Clonalities of 5 TCR Vβ repertoires were analyzed. Polyclonal repertoires were observed in 5 Vβ families (Vβ2, Vβ3, Vβ8.2, Vβ9, and Vβ11) before injection of AAT. Four weeks after initiation of AAT to prevent the development of diabetes, the clonal expanded repertoires were displayed in the same Vβ families (see FIG. 8).

Example 9

Procedures for Detecting and Quantitation of Clonality

Clonality of an expanded T-cell population in the CEDR3 region of 22 Vβ gene families can be detected using two-step PCR amplifications and subsequent detection by ultraviolet light after gel separation.

A first strand cDNA is synthesized by using either total RNA (oligodT primer is preferred) or mRNA using a random primer from human T-lymphocytes to serve as templates for primary PCR amplifications. Templates of the nested PCR are obtained from the PCR products of the primary amplification. Clonality of the TCR Vβ repertoires can be detected by separating the nested PCR products on high resolution agarose gel and directly observed under untraviolet light.

A typical procedure is outlined below:
Synthesize cDNA from T lymphocytes
Perform primary PCR amplification using H plate I pre-coated with primary primers for
    amplification of 22 Vβ families.
Perform nested PCR amplification using HC plate II pre-coated with nested primers for
    amplification of 22 Vβ families
    Test for presence of PCR products
    Determine clonality by separating PCR products on high resolution agarose gel Primary PCR Amplification Conditions:
Initial denaturation at 95° C. for 3 min, then
95° C. for 1 min
55° C. for 1 min
72° C. for 1 min
35 cycles
72° C. for 10 min
    Nested PCR Amplification Conditions:
Initial denaturation at 95° C. for 3 min, then
95° C. for 30 s
50° C. for 30 s
72° C. for 30 s
25 cycles
72° C. for 10 min
    Detecting Clonality
    Prepare a 4% high resolution agarose gel:
    HR agarose powder is mixed with 1× TAE buffer to the desired concentration and then heated in a microwave until completely melted. Ethidium bromide (final concentration 0.5 μg/ml) is added to the gel. After cooling the solution to about 60° C., it is poured into a 12-14 cm in length tray containing a sample comb with 24 teeth and allowed to solidify at room temperature.
    Load the nested PCR products and DNA marker into the gel:
    10 μl of a 10 bp DNA marker (provided by kit) are loaded into the first well. 10 μl of the nested PCR products from each sample (each Vβ family) tube is mixed with 1.5 μl of 6× loading buffer (provided by kit) and loaded into the sample wells.

Separate DNA Fragment by Electrophoresis:
    The PCR products can completely be separated by electrophoresis in 1× TAE buffer at 100 V for 1.5 to 2 hours (DNA fragment size of the PCR products of 22 Vβ gene families should be between 100 to 200 bp)
    Detect clonality of 22 TCR Vβ repertoire.
    Clonality of the TCR repertoire can be readily seen under UV light. Usually, there are three types of repertoires that can be seen in expanded T-cell populations. A monoclonal repertoire is observed as a single clear band. An oligoclonal repertoire appears as coupled clear bands and a Polyclonal repertoire as a smear.

Example 10

Detection and Quantitation of TCR Clonality in a Human Sample

Quantitative determination of clonality of expanded T-cell population in the CDR3 region of 22 TCR Vβ gene families can be performed by two step PCR amplifications, spectratyping, and quantitation with statistical analytical software. First strand cDNA is synthesized using either total RNA; e.g., with oligodT primer, or mRNA using a random primer from human T-lymphocytes to serve as templates for primary PCR amplifications. Templates of nested PCR are from the PCR products of the primary amplification. The amplified nested PCR fluorescently labeled products can be analyzed on a DNA sequencer (spectratyping) with GeneScan and Genotyper software after primary amplification. The extent of the clonal expansion can be quantitatively calculated by using the collected data from the spectratyping and statistical quantitative software (BioMed Immunotech, Inc., Alachua, Fla.)

Procedure:
Synthesize cDNA from T lymphocytes
Perform primary PCR amplification using H plate I (available from BioMed Immunotech, Inc.,
Alachua, Fla.) with pre-coated primary primers for amplifications of 22 Vβ families
Nested PCR amplification using HQ plate II (available from BioMed Immunotech, Inc.,
Alachua, Fla.) with pre-coated nested primers for amplifications of 22 Vβ families. 22 Vβ primers
    labeled with 6-FAM (florescence dye).
    Test for presence of PCR products.
    Spectratype using DNA sequencer with (e.g., GeneScan and Genotyper software)
Quantitative determination of clonality (software available from BioMed Immunotech, Inc.,
Alachua, Fla.)
    Nested PCR Amplification Conditions:
Initial denaturation at 95° C. for 3 min, then
95° C. for 30 s
55° C. for 30 s
72° C. for 30 s
25 cycles
72° C. for 10 min
    Spectratyping
    Samples for analysis on the DNA sequencer are prepared by adding 2 μl of (1:10) PCR product to 2 μl of loading buffer containing a 5/1/2 mix of formamide, Dextran Blue, and the internal size standard (red, ROX 400). The products are separated by electrophoresis on a 5.5% sequencing gel within a DNA sequencer and analyzed using software such as Genescan and Genotype.

Quantitative Determination of Clonality of Expanded T-Cell Clones

Quantitative determination of clonality of expanded T-cell population of 22 Vβ families can be performed by using analytical statistical quantitative software (BioMed Immunotech, Inc., Alachua, Fla.). There are two panels (control and testing panel) in the software. The Control panel is used to establish a standard distribution for each length of each Vβ family. An average distribution of each CDR3 length within the determined T-cell population is preferably from more than ten control subjects, which is used to perform PCR amplification and spectratyping under the same conditions as the tested samples. The extent of the clonal expansion is defined as a D (distance from mean value). D>3 SD (standard deviation) in each length of each family indicates significant changes.

Example 11

TCR Clonality Detection in Mouse Sample

Clonality of expanded T-cell population in CDR3 region of 22 Vβ gene families can be detected by two step PCR amplifications and directly viewed under UV light. First strand cDNA can be synthesized by using either total RNA (e.g., oligodT primer) or mRNA (random primer is preferred) from mouse T lymphocytes to serve as templates for primary PCR amplifications. Templates of the nested PCR are from the PCR products of the primary amplification. Clonality of the TCR Vβ repertoires can be detected by separating the nested PCR products on high resolution agarose gel and directly observed on UV light.

Procedure:
Synthesize cDNA from T lymphocytes
Primary PCR amplification using M plate I (available from BioMed Immunotech, Inc.,
  Alachua, Fla.) with pre-coated primary primers for amplifications of 22 Vβ families
Nested PCR amplification using MC plate II (available from BioMed Immunotech,
  Inc., Alachua, Fla.) with pre-coated nested primers for amplifications of 22 Vβ families
Test for PCR products
Determine Clonality (by Separating PCR Products on High Resolution Agarose Gel)
Primary PCR Amplifilcation Conditions:
Initial denaturation at 95° C. for 3 min, then
95° C. for 1 min
55° C. for 1 min
72° C. for 1 min
35 cycles
72° C. for 10 min
  Nested PCR Amplification Conditions:
Initial denaturation at 95° C. for 3 min, then 95° C. for 30 s
50° C. for 30 s
72° C. for 30 s
25 cycles
72° C. for 10 min
  Detecting Clonality:
1. Prepare 4% high resolution agarose gel: HR agarose powder is mixed with 1× TAE buffer to the desired concentration and then heated in a microwave until completely melted. Ethidium bromide (final concentration 0.5 µg/ml) is added to the gel. After cooling the solution to about 60° C., it is poured into a 12-14 cm in length tray containing a sample comb with 24 teeth and allowed to solidify at room temperature
2. Load the nested PCR products and DNA marker into the gel: 10 µl of 10 bp DNA marker are loaded into the first well. 10 µl of the nested PCR products from each sample (each Vβ family) tube are mixed with 1.5 µl of 6× loading buffer and loaded into the sample wells.
3. Separate DNA fragment by electrophoresis. The PCR products can be completely separated by electrophoresis in 1× TAE buffer at 100 V for 1.5 to 2 hours. DNA fragment size of the PCR products of 22 Vβ gene families should be between 100 to 200 bp.
4. Detecting clonality of 22 TCR Vβ repertoire
Clonality of the TCR repertoire can be readily seen under UV light. Usually, there are three types of repertoires seen in expanded T-cell populations.
  Monclonal repertoire—a single clear band
  Oligoclonal repertoire—couple clear bands
  Polyclonal repertoire—smear Example 12

TCR Quantitative Clonality Detection with Mouse Sample

The quantitative determination of clonality of expanded T-cell population in CDR3 region of 22 TCR Vβ gene families can be performed by two step PCR amplifications, spectratyping, and quantitation with statistical analytical software (BioMed Immunotech, Inc., Alachua, Fla.). First strand cDNA can be synthesized by using either total RNA (oligodT primer) or mRNA using a random primer from mouse T lymphocytes to serve as templates for primary PCR amplifications. Templates of nested PCR are obtained from the PCR products of the primary amplification. The amplified nested fluorescently labeled PCR products can be analyzed on DNA sequencer (spectratyping) with GeneScan and Genotyper software for primary amplification. The extent of the clonal expansion can be quantitatively calculated by using the collected data from the spectratyping and statistical quantitative software (BioMed Immunotech, Inc., Alachua, Fla.).

Procedure:
Synthesize cDNA from T lymphocytes
Primary PCR amplification using M plate I (available from
  BioMed Immunotech, Inc., Alachua, Fla.)
Nested PCR amplification using MQ plate II (available from
  BioMed Immunotech, Inc., Alachua, Fla.)
Test for presence of PCR products
Spectratype using DNA sequencer with GeneScan and
  Genotyper software (A&B Applied Biosystems, CA)
Quantitative determination of clonality using statistical quantitative software.
  Amplify 22 Vβ families with M plate I (available from BioMed Immunotech, Inc., Alachua, Fla.) with pre-coated primary primers.
  Amplify 22 Vβ families with pre-coated MQ plate II (available from BioMed Immunotech, Inc., Alachua, Fla.) nested primers labeled with 6-FAM (florescence dye).
Initial denaturation at 95° C. for 3 min, then 95° C. for 1 min
55° C. for 1 min
72° C. for 1 min
35 cycles
72° C. for 10 min
  Nested PCR amplification conditions:
Initial denaturation at 95° C. for 3 min, then
95° C. for 30 s
72° C. for 10 min
55° C. for 30 s
72° C. for 30 s
25 cycles
  Spectratyping
  Samples for analysis on the DNA sequencer are prepared by adding 2 µl of (1:10) PCR product to 2 µl of loading buffer containing a 5/1/2 mix of formamide, dextran blue, and the internal size standard (red, ROX 400). The products are separated by electrophoresis on a 5.5% sequencing gel within a DNA sequencer and analyzed using Genescan and Genotyper software.

Example 13

Statistical Analytical Quantitation of Clonality of Expanded T-cell Clones

Quantitative determination of clonality of expanded T-cell population of 22 Vβ families can be performed by using statistical quantitative software (BioMed Immunotech, Inc., Alachua, Fla.). There are two panels (control and testing panel) in the software. The Control panel is used to establish a standard distribution for each length of each Vβ family. An average distribution of each CDR3 length within the determined T-cell population is from more than ten control subjects, which will be used to perform PCR amplification and spectratyping under the same condition as the tested samples. The extent of the clonal expansion is defined as a D (distance from mean value). D>3 SD (standard deviation) in each length of each family indicate that there are significant changes.

Example 14

Detection Kits

The following tables illustrate several types of clonality detection kits. These exemplary kits are available from BioMed Immunotech, Inc., Inc. (Alachua, Fla.).

TABLE 2

Human Clonality Detection Kit:
Name

H Plate I
HC Plate II
Reaction buffer I
Reaction buffer II
HR agarose
6× DNA loading dye
Molecular grade water
10 bp DNA Marker
User manual

TABLE 3

Human Clonality Quantitation Kit:
Name

H Plate I
HQ Plate II
Reaction buffer I
Reaction buffer II
Molecular grade water
Quantitative software
User manual

TABLE 4

Mouse Clonality Detection Kit:
Name

M Plate I
MC Plate II
Reaction buffer I
Reaction buffer II
HR agarose
6× DNA loading dye
Molecular grade water
10 bp DNA Marker
User manual

TABLE 5

Human Clonality Quantitation Kit:
Name

M Plate I
MQ Plate II
Reaction buffer I
Reaction buffer II
Molecular grade water
Quantitative software
User manual

What is claimed is:

1. A kit for detecting human T-cell receptor (TCR) Vβ repertoires, comprising:
a group of 59 DNA primers each specific for one of 22 regions of T-cell Vβ gene CDR3 regions, said primers consisting of SEQ ID NOs: 60-118; and
instructions for use.

2. The kit of claim 1 further comprising analytical statistical software for quantitation of the detected TCR Vβ repertoires and additional instructions therefor.

3. The kit of claim 1 further comprising amplification buffers.

4. The kit of claim 1 further comprising a human T-lymphocyte containing tissue or fluid sample.

5. The kit of claim 4 wherein the T-lymphocyte tissue or fluid sample is a peripheral blood mononucleotide cell (PBMC).

6. A kit for detecting human T-cell receptor (TCR) Vβ repertoires, comprising:

a group of 36 DNA primers each specific for one of 22 regions of T-cell Vβ gene CDR3 regions, said group of primers consisting of SEQ ID NOs: 81, and 84-118; and
instructions for use.

7. The kit of claim 6 further comprising analytical statistical software for quantitation of the detected TCR Vβ repertoires and additional instructions therefor.

8. The kit of claim 6 further comprising amplification buffers.

9. The kit of claim 6 wherein each of the 36 primers is fluorescently labeled with 6 FAM.

10. The kit of claim 9 wherein the 36 fluorescently labeled primers are immobilized on a plate.

* * * * *

SEQUENCE LISTING

<160> NUMBER OF SEQ ID NOS: 118

<210> SEQ ID NO 1
<211> LENGTH: 25
<212> TYPE: DNA
<213> ORGANISM: Mus sp.

<400> SEQUENCE: 1
ccagagctca tgtttctcta caatc                25

<210> SEQ ID NO 2
<211> LENGTH: 21
<212> TYPE: DNA
<213> ORGANISM: Mus sp.

```
<400> SEQUENCE: 2
gttttatacc tgaatgccca g                                         21

<210> SEQ ID NO 3
<211> LENGTH: 25
<212> TYPE: DNA
<213> ORGANISM: Mus sp.

<400> SEQUENCE: 3
ctcttcccgg tgctgattac ctggc                                     25

<210> SEQ ID NO 4
<211> LENGTH: 19
<212> TYPE: DNA
<213> ORGANISM: Mus sp.

<400> SEQUENCE: 4
gctgcaagtg gccaacatg                                            19

<210> SEQ ID NO 5
<211> LENGTH: 26
<212> TYPE: DNA
<213> ORGANISM: Mus sp.

<400> SEQUENCE: 5
ctttcagaat caagaagttc ttcagc                                    26

<210> SEQ ID NO 6
<211> LENGTH: 21
<212> TYPE: DNA
<213> ORGANISM: Mus sp.

<400> SEQUENCE: 6
gtgtccttca aactcacctt g                                         21

<210> SEQ ID NO 7
<211> LENGTH: 25
<212> TYPE: DNA
<213> ORGANISM: Mus sp.

<400> SEQUENCE: 7
gtttcttctc agatcctcta aaacc                                     25

<210> SEQ ID NO 8
<211> LENGTH: 20
<212> TYPE: DNA
<213> ORGANISM: Mus sp.

<400> SEQUENCE: 8
cagatcacag ctctaaagcc                                           20

<210> SEQ ID NO 9
<211> LENGTH: 26
<212> TYPE: DNA
<213> ORGANISM: Mus sp.

<400> SEQUENCE: 9
ggcctggtat caacagactc aggggc                                    26

<210> SEQ ID NO 10
<211> LENGTH: 24
<212> TYPE: DNA
<213> ORGANISM: Mus sp.
```

<400> SEQUENCE: 10
gtttcttcac cgatagtcgg gtgc                                          24

<210> SEQ ID NO 11
<211> LENGTH: 27
<212> TYPE: DNA
<213> ORGANISM: Mus sp.

<400> SEQUENCE: 11
caggattcag ggaaaggatt gagactg                                       27

<210> SEQ ID NO 12
<211> LENGTH: 22
<212> TYPE: DNA
<213> ORGANISM: Mus sp.

<400> SEQUENCE: 12
cgtctcgaga gaagaagtca tc                                            22

<210> SEQ ID NO 13
<211> LENGTH: 26
<212> TYPE: DNA
<213> ORGANISM: Mus sp.

<400> SEQUENCE: 13
gctgatttat atctcatacg atgttg                                        26

<210> SEQ ID NO 14
<211> LENGTH: 19
<212> TYPE: DNA
<213> ORGANISM: Mus sp.

<400> SEQUENCE: 14
gcatttctcc ctgattctg                                                19

<210> SEQ ID NO 15
<211> LENGTH: 22
<212> TYPE: DNA
<213> ORGANISM: Mus sp.

<400> SEQUENCE: 15
gatgggtaca aggcctccag ac                                            22

<210> SEQ ID NO 16
<211> LENGTH: 21
<212> TYPE: DNA
<213> ORGANISM: Mus sp.

<400> SEQUENCE: 16
ctctctcatt ctggagttgg c                                             21

<210> SEQ ID NO 17
<211> LENGTH: 24
<212> TYPE: DNA
<213> ORGANISM: Mus sp.

<400> SEQUENCE: 17
gcactcagaa agcagatatc cctg                                          24

<210> SEQ ID NO 18
<211> LENGTH: 20
<212> TYPE: DNA
<213> ORGANISM: Mus sp.

-continued

```
<400> SEQUENCE: 18
ccagaccaag ccaagagaac                                              20

<210> SEQ ID NO 19
<211> LENGTH: 25
<212> TYPE: DNA
<213> ORGANISM: Mus sp.

<400> SEQUENCE: 19
gcatgggctg aggctgatcc attac                                        25

<210> SEQ ID NO 20
<211> LENGTH: 20
<212> TYPE: DNA
<213> ORGANISM: Mus sp.

<400> SEQUENCE: 20
gtccctgatg ggtacaaggc                                              20

<210> SEQ ID NO 21
<211> LENGTH: 24
<212> TYPE: DNA
<213> ORGANISM: Mus sp.

<400> SEQUENCE: 21
gattttgaac agggaagctg acac                                         24

<210> SEQ ID NO 22
<211> LENGTH: 19
<212> TYPE: DNA
<213> ORGANISM: Mus sp.

<400> SEQUENCE: 22
ctgctctctc tacattggc                                               19

<210> SEQ ID NO 23
<211> LENGTH: 28
<212> TYPE: DNA
<213> ORGANISM: Mus sp.

<400> SEQUENCE: 23
gaagattatg tttagctaca ataataag                                     28

<210> SEQ ID NO 24
<211> LENGTH: 21
<212> TYPE: DNA
<213> ORGANISM: Mus sp.

<400> SEQUENCE: 24
gctcatttga atcttcgaat c                                            21

<210> SEQ ID NO 25
<211> LENGTH: 26
<212> TYPE: DNA
<213> ORGANISM: Mus sp.

<400> SEQUENCE: 25
tgcagggcct ggagttcctg acttac                                       26

<210> SEQ ID NO 26
<211> LENGTH: 20
<212> TYPE: DNA
<213> ORGANISM: Mus sp.
```

```
<400> SEQUENCE: 26
ctcagctcag atgcccaatc                                              20

<210> SEQ ID NO 27
<211> LENGTH: 26
<212> TYPE: DNA
<213> ORGANISM: Mus sp.

<400> SEQUENCE: 27
cgcagcaagt ctcttatgga agatgg                                       26

<210> SEQ ID NO 28
<211> LENGTH: 20
<212> TYPE: DNA
<213> ORGANISM: Mus sp.

<400> SEQUENCE: 28
tccactctga agattcaacc                                              20

<210> SEQ ID NO 29
<211> LENGTH: 26
<212> TYPE: DNA
<213> ORGANISM: Mus sp.

<400> SEQUENCE: 29
tggacatgat acctttact ggtatc                                        26

<210> SEQ ID NO 30
<211> LENGTH: 20
<212> TYPE: DNA
<213> ORGANISM: Mus sp.

<400> SEQUENCE: 30
tcgattttct gctgtgaggc                                              20

<210> SEQ ID NO 31
<211> LENGTH: 29
<212> TYPE: DNA
<213> ORGANISM: Mus sp.

<400> SEQUENCE: 31
aaatcaagcc ctaacctcta ctggtactg                                    29

<210> SEQ ID NO 32
<211> LENGTH: 20
<212> TYPE: DNA
<213> ORGANISM: Mus sp.

<400> SEQUENCE: 32
acgaccaatt catcctaagc                                              20

<210> SEQ ID NO 33
<211> LENGTH: 25
<212> TYPE: DNA
<213> ORGANISM: Mus sp.

<400> SEQUENCE: 33
gtttctttct cagarcctcc aggac                                        25

<210> SEQ ID NO 34
<211> LENGTH: 23
<212> TYPE: DNA
<213> ORGANISM: Mus sp.
```

```
<400> SEQUENCE: 34
cccatcagtc atcccaactt atc                                      23

<210> SEQ ID NO 35
<211> LENGTH: 26
<212> TYPE: DNA
<213> ORGANISM: Mus sp.

<400> SEQUENCE: 35
tcatggagaa gtctaaactg tttaag                                   26

<210> SEQ ID NO 36
<211> LENGTH: 25
<212> TYPE: DNA
<213> ORGANISM: Mus sp.

<400> SEQUENCE: 36
gtttcttcac agtgagccgg gtgcc                                    25

<210> SEQ ID NO 37
<211> LENGTH: 30
<212> TYPE: DNA
<213> ORGANISM: Mus sp.

<400> SEQUENCE: 37
cacactgcct tttactggta tcaacagaac                               30

<210> SEQ ID NO 38
<211> LENGTH: 26
<212> TYPE: DNA
<213> ORGANISM: Mus sp.

<400> SEQUENCE: 38
gtttcttatt accaaaagcc tggtgc                                   26

<210> SEQ ID NO 39
<211> LENGTH: 25
<212> TYPE: DNA
<213> ORGANISM: Mus sp.

<400> SEQUENCE: 39
atggcaactg caaatgaagg ctctg                                    25

<210> SEQ ID NO 40
<211> LENGTH: 20
<212> TYPE: DNA
<213> ORGANISM: Mus sp.

<400> SEQUENCE: 40
cattctcaac gttgacagtg                                          20

<210> SEQ ID NO 41
<211> LENGTH: 25
<212> TYPE: DNA
<213> ORGANISM: Mus sp.

<400> SEQUENCE: 41
gtttcttgag tctggttcct ttacc                                    25

<210> SEQ ID NO 42
<211> LENGTH: 20
<212> TYPE: DNA
<213> ORGANISM: Mus sp.
```

<400> SEQUENCE: 42
ccatagagat ccagtccagc        20

<210> SEQ ID NO 43
<211> LENGTH: 26
<212> TYPE: DNA
<213> ORGANISM: Mus sp.

<400> SEQUENCE: 43
tgtatccctg aaaagggca cactgc        26

<210> SEQ ID NO 44
<211> LENGTH: 20
<212> TYPE: DNA
<213> ORGANISM: Mus sp.

<400> SEQUENCE: 44
gcctgggaat cagaacgtgc        20

<210> SEQ ID NO 45
<211> LENGTH: 25
<212> TYPE: DNA
<213> ORGANISM: Mus sp.

<400> SEQUENCE: 45
cacccaccag ctcagctcca cgtgg        25

<210> SEQ ID NO 46
<211> LENGTH: 27
<212> TYPE: DNA
<213> ORGANISM: Mus sp.

<400> SEQUENCE: 46
gtttcttctg cttttgatgg ctcaaac        27

<210> SEQ ID NO 47
<211> LENGTH: 25
<212> TYPE: DNA
<213> ORGANISM: Mus sp.

<400> SEQUENCE: 47
gtttcttcag ctttgagcct tcacc        25

<210> SEQ ID NO 48
<211> LENGTH: 20
<212> TYPE: DNA
<213> ORGANISM: Mus sp.

<400> SEQUENCE: 48
gttcctcgaa ctcacagtgc        20

<210> SEQ ID NO 49
<211> LENGTH: 25
<212> TYPE: DNA
<213> ORGANISM: Mus sp.

<400> SEQUENCE: 49
gtttcttcct tctccaaaat agagc        25

<210> SEQ ID NO 50
<211> LENGTH: 28
<212> TYPE: DNA
<213> ORGANISM: Mus sp.

```
<400> SEQUENCE: 50
agcttggtat cgtcaatcgc ctcaaaag                              28

<210> SEQ ID NO 51
<211> LENGTH: 25
<212> TYPE: DNA
<213> ORGANISM: Mus sp.

<400> SEQUENCE: 51
gtttcttgag tcgagtcccc tctcc                                 25

<210> SEQ ID NO 52
<211> LENGTH: 19
<212> TYPE: DNA
<213> ORGANISM: Mus sp.

<400> SEQUENCE: 52
ccaacccaca gcactggag                                        19

<210> SEQ ID NO 53
<211> LENGTH: 24
<212> TYPE: DNA
<213> ORGANISM: Mus sp.

<400> SEQUENCE: 53
gtttcttgac ggtgagtcgt gtcc                                  24

<210> SEQ ID NO 54
<211> LENGTH: 25
<212> TYPE: DNA
<213> ORGANISM: Mus sp.

<400> SEQUENCE: 54
ctttcagaat gaagacatca tcgac                                 25

<210> SEQ ID NO 55
<211> LENGTH: 25
<212> TYPE: DNA
<213> ORGANISM: Mus sp.

<400> SEQUENCE: 55
gtttcttcag tctggttcct gagcc                                 25

<210> SEQ ID NO 56
<211> LENGTH: 22
<212> TYPE: DNA
<213> ORGANISM: Mus sp.

<400> SEQUENCE: 56
ctcagtccaa cagtttgatg ac                                    22

<210> SEQ ID NO 57
<211> LENGTH: 25
<212> TYPE: DNA
<213> ORGANISM: Mus sp.

<400> SEQUENCE: 57
gtttcttgga gccgagtgcc tggcc                                 25

<210> SEQ ID NO 58
<211> LENGTH: 19
<212> TYPE: DNA
<213> ORGANISM: Mus sp.
```

```
<400> SEQUENCE: 58
cctcaagtcg cttccaacc                                           19

<210> SEQ ID NO 59
<211> LENGTH: 25
<212> TYPE: DNA
<213> ORGANISM: Mus sp.

<400> SEQUENCE: 59
gtttcttaac cgtgagcctg gtggc                                    25

<210> SEQ ID NO 60
<211> LENGTH: 21
<212> TYPE: DNA
<213> ORGANISM: Homo sapiens

<400> SEQUENCE: 60
gtgtactggt accaacagag c                                        21

<210> SEQ ID NO 61
<211> LENGTH: 22
<212> TYPE: DNA
<213> ORGANISM: Homo sapiens

<400> SEQUENCE: 61
gaacctctgt gaagatcgag tg                                       22

<210> SEQ ID NO 62
<211> LENGTH: 21
<212> TYPE: DNA
<213> ORGANISM: Homo sapiens

<400> SEQUENCE: 62
gtgtccagga tatggaccat g                                        21

<210> SEQ ID NO 63
<211> LENGTH: 22
<212> TYPE: DNA
<213> ORGANISM: Homo sapiens

<400> SEQUENCE: 63
gccaagtcac catgatgttc tg                                       22

<210> SEQ ID NO 64
<211> LENGTH: 21
<212> TYPE: DNA
<213> ORGANISM: Homo sapiens

<400> SEQUENCE: 64
cagtattatg agaaagaaga g                                        21

<210> SEQ ID NO 65
<211> LENGTH: 23
<212> TYPE: DNA
<213> ORGANISM: Homo sapiens

<400> SEQUENCE: 65
ctgaacacaa ccgcctttat tgg                                      23

<210> SEQ ID NO 66
<211> LENGTH: 23
<212> TYPE: DNA
<213> ORGANISM: Homo sapiens
```

```
<400> SEQUENCE: 66
caagacacct ggtcatggga atg                                              23

<210> SEQ ID NO 67
<211> LENGTH: 23
<212> TYPE: DNA
<213> ORGANISM: Homo sapiens

<400> SEQUENCE: 67
ctggtacaga cagaccatga tgc                                              23

<210> SEQ ID NO 68
<211> LENGTH: 22
<212> TYPE: DNA
<213> ORGANISM: Homo sapiens

<400> SEQUENCE: 68
ggtcacacag atgggaaacg ac                                               22

<210> SEQ ID NO 69
<211> LENGTH: 23
<212> TYPE: DNA
<213> ORGANISM: Homo sapiens

<400> SEQUENCE: 69
ggaatgttct caaaccatgg gcc                                              23

<210> SEQ ID NO 70
<211> LENGTH: 24
<212> TYPE: DNA
<213> ORGANISM: Homo sapiens

<400> SEQUENCE: 70
catgggctga ggctaatcca ttac                                             24

<210> SEQ ID NO 71
<211> LENGTH: 24
<212> TYPE: DNA
<213> ORGANISM: Homo sapiens

<400> SEQUENCE: 71
gcccaggata tgaaccataa ctac                                             24

<210> SEQ ID NO 72
<211> LENGTH: 23
<212> TYPE: DNA
<213> ORGANISM: Homo sapiens

<400> SEQUENCE: 72
gtcctggtat cgacaagacc cag                                              23

<210> SEQ ID NO 73
<211> LENGTH: 23
<212> TYPE: DNA
<213> ORGANISM: Homo sapiens

<400> SEQUENCE: 73
ggagagatct ctgatggata cag                                              23

<210> SEQ ID NO 74
<211> LENGTH: 24
<212> TYPE: DNA
<213> ORGANISM: Homo sapiens
```

<400> SEQUENCE: 74
caggatgagt ccggtatgcc caac                                        24

<210> SEQ ID NO 75
<211> LENGTH: 23
<212> TYPE: DNA
<213> ORGANISM: Homo sapiens

<400> SEQUENCE: 75
cagggcaagg gctgagattg atc                                         23

<210> SEQ ID NO 76
<211> LENGTH: 25
<212> TYPE: DNA
<213> ORGANISM: Homo sapiens

<400> SEQUENCE: 76
gtttactggt atcggcagct cccag                                       25

<210> SEQ ID NO 77
<211> LENGTH: 22
<212> TYPE: DNA
<213> ORGANISM: Homo sapiens

<400> SEQUENCE: 77
ggtattggcc agatcagctc tg                                          22

<210> SEQ ID NO 78
<211> LENGTH: 23
<212> TYPE: DNA
<213> ORGANISM: Homo sapiens

<400> SEQUENCE: 78
ggtgcaatcc tatttctggc cac                                         23

<210> SEQ ID NO 79
<211> LENGTH: 24
<212> TYPE: DNA
<213> ORGANISM: Homo sapiens

<400> SEQUENCE: 79
gacaggaagt gatcttgcgc tgtg                                        24

<210> SEQ ID NO 80
<211> LENGTH: 23
<212> TYPE: DNA
<213> ORGANISM: Homo sapiens

<400> SEQUENCE: 80
catccctgat cgattctcag ctc                                         23

<210> SEQ ID NO 81
<211> LENGTH: 25
<212> TYPE: DNA
<213> ORGANISM: Homo sapiens

<400> SEQUENCE: 81
gtttctttga gccgtgtccc tggcc                                       25

<210> SEQ ID NO 82
<211> LENGTH: 27
<212> TYPE: DNA
<213> ORGANISM: Homo sapiens

```
<400> SEQUENCE: 82
ctccgagagc ccgtagaact ggacttg                                    27

<210> SEQ ID NO 83
<211> LENGTH: 19
<212> TYPE: DNA
<213> ORGANISM: Homo sapiens

<400> SEQUENCE: 83
ttccctgact tgcactctg                                             19

<210> SEQ ID NO 84
<211> LENGTH: 25
<212> TYPE: DNA
<213> ORGANISM: Homo sapiens

<400> SEQUENCE: 84
gtttcttcac tgagagccgg gtccc                                      25

<210> SEQ ID NO 85
<211> LENGTH: 20
<212> TYPE: DNA
<213> ORGANISM: Homo sapiens

<400> SEQUENCE: 85
ccctgattct ggagtccgcc                                            20

<210> SEQ ID NO 86
<211> LENGTH: 19
<212> TYPE: DNA
<213> ORGANISM: Homo sapiens

<400> SEQUENCE: 86
gcccaaacct aacattctc                                             19

<210> SEQ ID NO 87
<211> LENGTH: 25
<212> TYPE: DNA
<213> ORGANISM: Homo sapiens

<400> SEQUENCE: 87
gtttcttcac caggagccgc gtgcc                                      25

<210> SEQ ID NO 88
<211> LENGTH: 18
<212> TYPE: DNA
<213> ORGANISM: Homo sapiens

<400> SEQUENCE: 88
ggatctttct ccaccttg                                              18

<210> SEQ ID NO 89
<211> LENGTH: 18
<212> TYPE: DNA
<213> ORGANISM: Homo sapiens

<400> SEQUENCE: 89
ctcacttatg ccttcacc                                              18

<210> SEQ ID NO 90
<211> LENGTH: 18
<212> TYPE: DNA
<213> ORGANISM: Homo sapiens
```

```
<400> SEQUENCE: 90
gcatcattct ccactctg                                            18

<210> SEQ ID NO 91
<211> LENGTH: 25
<212> TYPE: DNA
<213> ORGANISM: Homo sapiens

<400> SEQUENCE: 91
gtttcttgag ctgggttcca ctgcc                                    25

<210> SEQ ID NO 92
<211> LENGTH: 19
<212> TYPE: DNA
<213> ORGANISM: Homo sapiens

<400> SEQUENCE: 92
gacggagcat tttcccctg                                           19

<210> SEQ ID NO 93
<211> LENGTH: 25
<212> TYPE: DNA
<213> ORGANISM: Homo sapiens

<400> SEQUENCE: 93
gtttcttgag ccaacttccc tctcc                                    25

<210> SEQ ID NO 94
<211> LENGTH: 18
<212> TYPE: DNA
<213> ORGANISM: Homo sapiens

<400> SEQUENCE: 94
ccagatcaac cacagagg                                            18

<210> SEQ ID NO 95
<211> LENGTH: 19
<212> TYPE: DNA
<213> ORGANISM: Homo sapiens

<400> SEQUENCE: 95
caaccagacc tctctgtac                                           19

<210> SEQ ID NO 96
<211> LENGTH: 21
<212> TYPE: DNA
<213> ORGANISM: Homo sapiens

<400> SEQUENCE: 96
gtttcttgag tcgagtccca t                                        21

<210> SEQ ID NO 97
<211> LENGTH: 18
<212> TYPE: DNA
<213> ORGANISM: Homo sapiens

<400> SEQUENCE: 97
gagggacgta ttctactc                                            18

<210> SEQ ID NO 98
<211> LENGTH: 24
<212> TYPE: DNA
<213> ORGANISM: Homo sapiens
```

```
<400> SEQUENCE: 98
gtttcttaac ctggtccccg aacc                                              24

<210> SEQ ID NO 99
<211> LENGTH: 24
<212> TYPE: DNA
<213> ORGANISM: Homo sapiens

<400> SEQUENCE: 99
gtttcttgag cctggtgccc ggcc                                              24

<210> SEQ ID NO 100
<211> LENGTH: 18
<212> TYPE: DNA
<213> ORGANISM: Homo sapiens

<400> SEQUENCE: 100
gctccttctc agtgactc                                                     18

<210> SEQ ID NO 101
<211> LENGTH: 25
<212> TYPE: DNA
<213> ORGANISM: Homo sapiens

<400> SEQUENCE: 101
gtttcttgag tctggtgcct tgtcc                                             25

<210> SEQ ID NO 102
<211> LENGTH: 19
<212> TYPE: DNA
<213> ORGANISM: Homo sapiens

<400> SEQUENCE: 102
cagttgaaag gcctgatgg                                                    19

<210> SEQ ID NO 103
<211> LENGTH: 20
<212> TYPE: DNA
<213> ORGANISM: Homo sapiens

<400> SEQUENCE: 103
cagtgactat cattctgaac                                                   20

<210> SEQ ID NO 104
<211> LENGTH: 19
<212> TYPE: DNA
<213> ORGANISM: Homo sapiens

<400> SEQUENCE: 104
gccgaacact tctttctgc                                                    19

<210> SEQ ID NO 105
<211> LENGTH: 27
<212> TYPE: DNA
<213> ORGANISM: Homo sapiens

<400> SEQUENCE: 105
gtttcttaaa cacagcgacc tcgggtg                                           27

<210> SEQ ID NO 106
<211> LENGTH: 20
<212> TYPE: DNA
<213> ORGANISM: Homo sapiens
```

-continued

```
<400> SEQUENCE: 106
gaaaggagta gactccactc                                              20

<210> SEQ ID NO 107
<211> LENGTH: 20
<212> TYPE: DNA
<213> ORGANISM: Homo sapiens

<400> SEQUENCE: 107
ggaatccttt cctctcactg                                              20

<210> SEQ ID NO 108
<211> LENGTH: 19
<212> TYPE: DNA
<213> ORGANISM: Homo sapiens

<400> SEQUENCE: 108
ggagtcgcta ccagctccc                                               19

<210> SEQ ID NO 109
<211> LENGTH: 19
<212> TYPE: DNA
<213> ORGANISM: Homo sapiens

<400> SEQUENCE: 109
cagttccaaa tcgcttctc                                               19

<210> SEQ ID NO 110
<211> LENGTH: 18
<212> TYPE: DNA
<213> ORGANISM: Homo sapiens

<400> SEQUENCE: 110
caggctaaat tctccctg                                                18

<210> SEQ ID NO 111
<211> LENGTH: 25
<212> TYPE: DNA
<213> ORGANISM: Homo sapiens

<400> SEQUENCE: 111
gtttcttgag cctggtcccg ttccc                                        25

<210> SEQ ID NO 112
<211> LENGTH: 22
<212> TYPE: DNA
<213> ORGANISM: Homo sapiens

<400> SEQUENCE: 112
gaaagccagt gaccctgagt tg                                           22

<210> SEQ ID NO 113
<211> LENGTH: 18
<212> TYPE: DNA
<213> ORGANISM: Homo sapiens

<400> SEQUENCE: 113
agtgcccatc ctgaagac                                                18

<210> SEQ ID NO 114
<211> LENGTH: 25
<212> TYPE: DNA
<213> ORGANISM: Homo sapiens
```

```
<400> SEQUENCE: 114
gtttcttcag cctagagcct tctcc                                          25

<210> SEQ ID NO 115
<211> LENGTH: 25
<212> TYPE: DNA
<213> ORGANISM: Homo sapiens

<400> SEQUENCE: 115
gtttcttact gtcagccggg ttgcc                                          25

<210> SEQ ID NO 116
<211> LENGTH: 19
<212> TYPE: DNA
<213> ORGANISM: Homo sapiens

<400> SEQUENCE: 116
gtgaacgcct tgttgctgg                                                 19

<210> SEQ ID NO 117
<211> LENGTH: 19
<212> TYPE: DNA
<213> ORGANISM: Homo sapiens

<400> SEQUENCE: 117
gtgcgaggag attcggcag                                                 19

<210> SEQ ID NO 118
<211> LENGTH: 25
<212> TYPE: DNA
<213> ORGANISM: Homo sapiens

<400> SEQUENCE: 118
gtttcttcac ggtcagcctg ctgcc                                          25
```